(12) United States Patent
Jaeger

(10) Patent No.: US 10,945,640 B2
(45) Date of Patent: Mar. 16, 2021

(54) METHOD AND APPARATUS FOR TRACKING LIQUID CONSUMPTION BEHAVIOR

(71) Applicant: Bradley Jaeger, Ferndale, MI (US)

(72) Inventor: Bradley Jaeger, Ferndale, MI (US)

(*) Notice: Subject to any disclaimer, the term of this patent is extended or adjusted under 35 U.S.C. 154(b) by 385 days.

(21) Appl. No.: 15/433,975

(22) Filed: Feb. 15, 2017

(65) Prior Publication Data

US 2017/0231527 A1    Aug. 17, 2017

Related U.S. Application Data

(60) Provisional application No. 62/295,317, filed on Feb. 15, 2016.

(51) Int. Cl.
| | |
|---|---|
| *A61B 5/11* | (2006.01) |
| *A61B 5/00* | (2006.01) |
| *G01C 19/00* | (2013.01) |
| *G01P 15/18* | (2013.01) |

(52) U.S. Cl.
CPC .............. *A61B 5/11* (2013.01); *A61B 5/4833* (2013.01); *G01C 19/00* (2013.01); *G01P 15/18* (2013.01)

(58) Field of Classification Search
CPC ....... A61B 5/11; A61B 5/4833; A61B 5/1114; A61B 5/6824; A61B 5/1123; G01C 19/00; G01P 15/18
See application file for complete search history.

(56) References Cited

U.S. PATENT DOCUMENTS

| | | | | |
|---|---|---|---|---|
| 2010/0103108 A1* | 4/2010 | Hotelling | .............. | G06F 1/3215 345/166 |
| 2014/0372045 A1* | 12/2014 | Keski-Pukkila | ..... | A61B 5/6887 702/19 |
| 2014/0377724 A1* | 12/2014 | Hoover | .............. | G06K 9/00355 434/127 |
| 2015/0050630 A1* | 2/2015 | Hanlon | .................... | G09B 5/02 434/262 |
| 2015/0379238 A1* | 12/2015 | Connor | ............... | G06F 19/3475 702/19 |
| 2016/0242680 A1* | 8/2016 | Arif | ...................... | A61B 5/1112 |

FOREIGN PATENT DOCUMENTS

| | | | |
|---|---|---|---|
| JP | 2006039971 A | * | 2/2006 |
| JP | 2014079506 A | * | 5/2014 |

* cited by examiner

*Primary Examiner* — Mohamed Charioui
*Assistant Examiner* — Eyob Hagos
(74) *Attorney, Agent, or Firm* — Woods Rogers PLC; Nathan A. Evans

(57) ABSTRACT

A method of detecting, measuring, logging, and tracking a user's consumption of liquid through an electronic wearable on a person's wrist, hand, or other extremity used for consuming beverages is described. In preferred embodiments, the electronic wearable can detect individual sips, the final sip of a beverage, and the type of container the beverage is being consumed from.

26 Claims, 24 Drawing Sheets

Preferred Embodiment

Simplest Embodiment

Embodiment w/ options

The Eight Step Consumption Process

METHOD AND APPARATUS FOR TRACKING LIQUID CONSUMPTION BEHAVIOR

BACKGROUND OF THE INVENTION

Field of the Invention

The present invention is directed to a method of detecting, measuring, logging, and tracking a user's consumption of liquid through an electronic wearable on a person's wrist, hand, or other extremity used for consuming beverages.

Description of the Related Art

Logging consumption of food or liquids has been a common practice for athletes attempting to maximize training and performance results, as well as non-athletes on a diet trying to either live a healthier lifestyle or lose weight. With the invention of smartphones, tablets, and laptops, logging food and liquid consumption have become easier with software dedicated to these specific tasks. Regarding fluid specifically, existing phone apps help users log their fluid intake to, for example, ensure proper hydration, monitor estimated blood alcohol levels, and avoid ingesting too much caffeine.

A new generation of wearable electronic devices now allows even more convenient means of tracking dietary and fitness levels. Certain wearable electronic fitness trackers advertise dietary logging including food, water, and caffeine. However, these devices require the user to input information (e.g., type and amount of beverage), rather than having that information tracked automatically through recognition of consumption by the device itself. The problem with prior art tracking mechanisms is their inherent need for the user to manually enter the type of drink, the amount consumed, and the time either when the consumption is taking place or at a later time with a time stamp back to when the consumption took place, which ultimately leads to non-compliance with dietary or athletic performance goals.

U.S. patent application US 2014/0372045, for example, attempts to resolve the problem of requiring manual input of liquid consumption by teaching an electronic band that attaches to a fluid container and records drinking events through the sensors embedded in the band. This information and data collected from the band is relayed to a smartphone or tablet via wireless communication means, where the information is analyzed by a processor. While this invention eliminates the need for the user to enter each sip of water or other type of drink consumed, it inconveniently requires the user to carry around a band and sensor specifically to place on each container the user drinks from whenever and wherever the user drinks throughout the course of days or weeks to achieve desired fitness or dietary results. That invention also requires the need for the user to enter information about the container the user is consuming a beverage from, which, as with any constant need for data entry, can be burdensome.

Thus, the need exists for a wearable electronic device that can detect the consumption of a beverage by a user with less, limited, or no manual input from said user into an application or physical notebook. The wearable electronic device and/or method of tracking drinking behavior become more useful if they can detect the type of fluid container the beverage is being consumed from, and ultimately detect the type of fluid being consumed. This eliminates the need for the user to keep track of beverage consumption by memory, manual logging, or digital logging.

SUMMARY OF THE INVENTION

An object of this invention is to detect and monitor liquid consumption through the use of a wearable electronic device, without the need for an electronic device to be placed around the drinking apparatus, or for burdensome data entry. The results of information and data received from each consumption process and multiple consumption processes over time can be analyzed by a program or programs on the wearable device or some other electronic device linked to the wearable device to track consumption, extrapolate results to the dietary or athletic goals of a user, or otherwise analyze the drinking patterns of a user and the results thereof.

Another object of this invention is to detect and record what kind of container the user is drinking from in which the liquid is contained (e.g., a bottle, a can, a mug, etc.), which information may be used in the downstream analysis of the results of a user's drinking behavior.

Another object of this invention is to detect and isolate a consumption process based on hand gestures compared to other hand movements, allowing tracking of drinking as opposed to other tasks, (e.g., writing, eating, and other tasks involving the hands), in order to both monitor fluid intake and determine certain properties of the liquid's container.

Another object of this invention is to provide nutritional information to the user based on the amount and type of liquid consumed, including the amount and type of liquid consumed over set periods of time (e.g., one day, one week, one month, one year, and so on).

In one embodiment of the present invention, an arm, hand, or wrist bracelet or band with electronic features (e.g., a wearable device) will be worn around the wrist of a user. This wearable should have at least one sensor capable of measuring accelerations, motions, or position/attitude of the wrist and/or hand. A microprocessor receives information collected by the sensor(s) and processes that information. In a preferred embodiment, the wearable contains memory storage capability to store the processed data collected by the sensor(s). The wearable should have a means of communicating with a phone, tablet, computer, other peripheral device, or the internet. This communication can be achieved through a radio frequency (rf) signal like Bluetooth or but this can also be done through a physical cable such as a USB cable. The preferred embodiment will use Bluetooth to communicate with a smartphone and software on said smartphone. The wearable can also include a display to communicate necessary information to the user or a touch screen, similar to a smart watch (e.g., an Apple Watch®) to allow the user to both see and input information. The wearable can also contain multiple physical or digital buttons to input information.

In preferred embodiments, the microprocessor will have an algorithm programmed into it that will be able to recognize a prescribed set of motions through accelerometer(s) in the wearable which will detect and isolate the consumption process from all other hand movements and gestures. This desired result can also be achieved with a gyroscope in the wearable device. Once the event is recognized, the microprocessor will be able to save important data to the memory on the wearable device, or externally. By analyzing the data of the consumption processes, the amount of liquid, type and/or size of the container, and other information, will be determined. When combined with information about the type of liquid consumed, as processed by the microprocessor or other processing means, the user will be able to see nutritional information about what they have consumed such as amount of water, caffeine, sugar, alcohol, and other figures. This will allow the user to track fluid intake, and use that data to compare against dietary and/or athletic goals, or to maximize drinking behavior to result in improved dietary, physical, and/or mental health.

Specific aspects of the current invention include Aspect 1, which is a method of determining whether a user is drinking liquid, the method comprising: measuring changes to the x, y, or z axes using an accelerometer or gyroscope located on a wearable electronic device; measuring changes to the total g force using an accelerometer on said wearable electronic device; having a microprocessor analyze data from x, y, or z axes along with total g forces to determine if the changes indicate the user of the wearable electronic device is drinking.

Aspect 2 is the method of Aspect 1 wherein one or more of the following steps are detected to thereby indicate whether the user is drinking:
a. Reaching for drink;
b. Grabbing drink;
c. Lifting drink to mouth;
d. Tilting until liquid touches lips;
e. Tilting while consuming;
f. "Unfitting" (or reversing the drinking tilt) to normal holding position;
g. Lowering drink; and
h. Returning drink and arm.

Aspect 3 is a method of determining whether a wearer of an electronic device having an accelerometer or gyroscope is drinking based on changes to the x, y, and/or z axes and total g forces indicates the wearer is reaching for a drink.

Aspect 4 is a method of determining if a wearer of an electronic device having an accelerometer or gyroscope is drinking based on whether changes to the x, y, and/or z axes and total g forces indicate the wearer is grabbing a drink.

Aspect 5 is a method of determining if a wearer of an electronic device having an accelerometer or gyroscope is drinking based on whether changes to the x, y, and/or z axes and total g forces indicate the wearer is lifting the drink to the wearer's mouth.

Aspect 6 is a method of determining if a wearer of an electronic device having an accelerometer or gyroscope is drinking based on whether changes to the x, y, and/or z axes and total g forces indicate the wearer is tilting the drink until the liquid touches the wearer's lips.

Aspect 7 is a method of determining if a wearer of an electronic device having an accelerometer or gyroscope is drinking based on whether changes to the x, y, and/or z axes and total g forces indicate the wearer is tilting the drink to consume it.

Aspect 8 is a method of determining if a wearer of an electronic device having an accelerometer or gyroscope is drinking based on whether changes to the x, y, and/or z axes and total g forces indicate the wearer is untilting the drink back to a normal holding position.

Aspect 9 is a method of determining if a wearer of an electronic device having an accelerometer or gyroscope is drinking based on whether changes to the x, y, and/or z axes and total g forces indicate the wearer is lowering the drink.

Aspect 10 is a method of determining if a wearer of an electronic device having an accelerometer or gyroscope is drinking based on whether changes to the x, y, and/or z axes and total g forces indicate the wearer is returning the drink to a resting position.

Aspect 11 is a method of determining whether a wearer of an electronic device having an accelerometer or gyroscope is drinking based on changes to the x, y, and/or z axes and total g forces, as measured by the accelerometer or gyroscope, indicating the wearer is performing two or more of the following actions:
1. Reaching for drink;
2. Grabbing drink;
3. Lifting drink to mouth;
4. Tilting until liquid touches lips;
5. Tilting while consuming;
6. "Untilting" (or reversing the drinking tilt) to normal holding position;
7. Lowering drink; and
8. Returning drink and arm.

Aspect 12 is a method of determining whether a wearer of an electronic device having an accelerometer or gyroscope has taken the last sip of a beverage from a drinking container based on measured changes to the x, y, and/or z axes using said accelerometer or gyroscope.

Aspect 13 is a method of determining whether a wearer of an electronic device having an accelerometer or gyroscope has taken the last sip of a beverage from a drinking container based on measured changes to the x, y, and/or z axes along with measured total g forces using said accelerometer or gyroscope.

Aspect 14 is a method of tracking drinking behavior comprising: using a wearable electronic device to detect changes in the x, y, or z axis, along with changes in g forces; and using a microprocessor to analyze the measured drinking behavior.

Aspect 15 is a method of tracking drinking behavior comprising: using a wearable electronic device to detect changes in the x, y, or z axis, along with changes in g forces; using a microprocessor to analyze the measured drinking behavior; and outputting to the user the results of the analysis.

Aspect 16 is a method of tracking drinking behavior comprising: using a wearable electronic device to detect changes in the x, y, or z axis, along with changes in g forces; using a microprocessor to analyze the measured drinking behavior; and outputting to the user consequences of the drinking behavior based on metrics related to physical performance, as well as physical and mental health issues impacted by drinking behavior.

Aspect 17 is a method of determining the type of container from which a wearer of a wearable electronic device is drinking comprising: logging the peak x axis accelerations during the consumption phase; and running a regression on said peak x axis acceleration points in order to classify the type of container based on set parameters and other previous data from user.

Aspect 18 is a method of determining the type of container from an electronic device placed on a beverage container with a sensor or sensors being consumed comprising: logging the peak x axis accelerations during the consumption phase; and running a regression on said peak x axis acceleration points in order to classify the type of container based on set parameters and other previous data from user.

Aspect 19 is a method of determining whether a person is drinking a beverage by using an electronic device placed on a beverage container having a gyroscope based on measured changes to the x, y, and/or z axes using said gyroscope.

Aspect 20 is a method of determining Whether a person has consumed the last sip of a beverage by using an electronic device placed on the beverage container having an accelerometer or gyroscope based on measured changes to the x, y, and/or z axes, and by comparing measurements to previous peak accelerations seen during the consumption phase.

Aspect 21 is a method for determining whether a user is consuming a fluid through use of an electronic device capable of being attached to or worn on an extremity of a user, comprising:

A first motion sensor capable of detecting movement, position, and/or orientation located within a housing for the portable electronic device, and A microprocessor capable of receiving, interpreting, and analyzing signals from said motion sensor and able to run programmed algorithms, and An algorithm capable of detecting when said user consumes a liquid by recognizing specific gestures (movements and change in position and/or orientation) and capable to filtering out other non-drinking movements.

Aspect 22 is a method of Aspect 21, wherein the motion sensor is an accelerometer and the method of determining whether a user is consuming fluid is by comparing total accelerations to the individual accelerations of axes and/or position/orientation of said user's wrist/hand.

Aspect 23 is a method of Aspect 21, wherein the motion sensor is a gyroscope and the method of determining whether a user is consuming fluid is by analyzing the specific orientation and position of said user's hand/arm/extremity.

Aspect 24 is a method of Aspect 21, wherein the detection algorithm detects the consumption portion of the consumption process by comparing overall movement of user's extremity to changes in position and/or orientation of said extremity.

Aspect 25 is a method of Aspect 24, wherein a change in position and/or orientation is determined by monitoring the pitch angle (rotation about the axis parallel to said user's forearm).

Aspect 26 is a method of Aspect 24, wherein a change in position and/or orientation is determined by monitoring the x axis acceleration and the total acceleration of said extremity Aspect 27 is a method of Aspect 24, wherein a change in position and/or orientation is determined by using a gyroscope.

BRIEF DESCRIPTION OF THE DRAWINGS

The accompanying drawings illustrate certain aspects of embodiments of the present invention, and should not be used to limit the invention. Together with the written description the drawings serve to explain certain principles of the invention. A wide variety of potential embodiments will be more readily understood through the following detailed description of certain exemplary embodiments, with reference to the accompanying exemplary drawings in which.

DETAILED DESCRIPTION OF VARIOUS EMBODIMENTS OF THE INVENTION

Reference will now be made in detail to various exemplary embodiments of the invention. It is to be understood that the following discussion of exemplary embodiments is not intended as a limitation on the invention. Rather, the following discussion is provided to give the reader a more detailed understanding of certain aspects and features of the invention.

Figure 1:
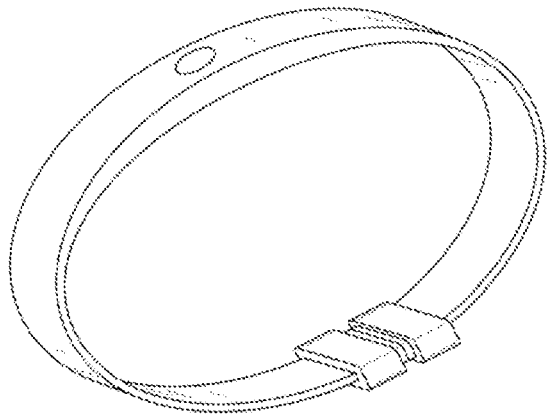
FIG. 1 shows an example of a preferred embodiment of the wearable electronic device.

FIG. 1 shows an example of a wearable electronic device, which, in a preferred embodiment includes an accelerometer for detecting movement, as well as processing capability to monitor, record, and analyze drinking activity. The preferred location for the wearable electronic device is on the wrist (as pictured), but it could also be worn, for example, on a finger, on a hand, or further up the arm if arranged differently and able to detect drinking activity as disclosed herein. The exemplary wearable electronic device consists of a band to be worn around the wrist of the user. This band can be constructed of any material that will secure the wearable electronic device to the user including but not limited to rubber, leather, plastic, metal (aluminum, titanium, steal, etc.), neoprene, or any other material which would not interfere with the invention disclosed in this patent application. The housing may, by way of example, contain the electronic portion of the wearable electronic device such as the power source, microprocessor, sensor, data storage, communication chip, etc., although these functions may be performed by electronics in the band or even external of the wearable device. The housing can be a separate portion that connects to the band, or it can be contained inside of the band.

In a preferred embodiment, the wearable electronic device includes a first sensor that comprises a three-axis accelerometer. The first sensor could also comprise a gyroscope. With both of these sensors, three-axis sensors are preferred, but could consist of a single axis sensor. The wearable electronic device may also include a second sensor, which, in an embodiment, would comprise the combination of both an accelerometer and a gyroscope. When the term "motion sensor" is used herein, it is referencing an accelerometer, gyroscope, or other sensor capable of detecting linear or rotational movements along or around at least one axis.

Figure 4:
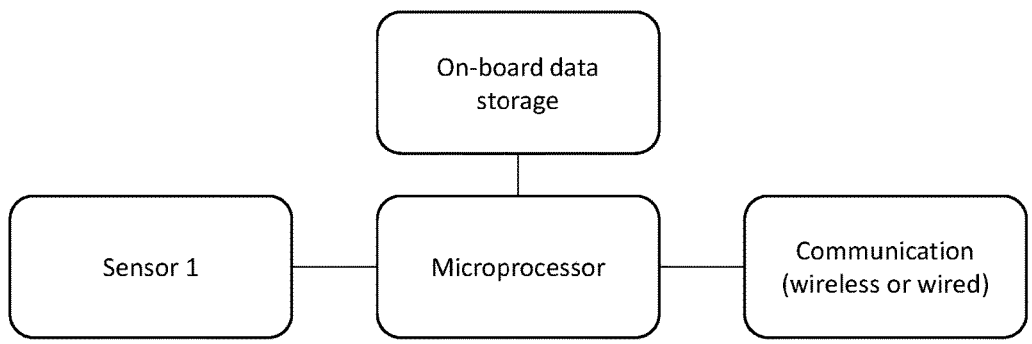
FIG. 4 illustrates the electrical components of the wearable electronic device in its most simplistic state.
Figure 5:
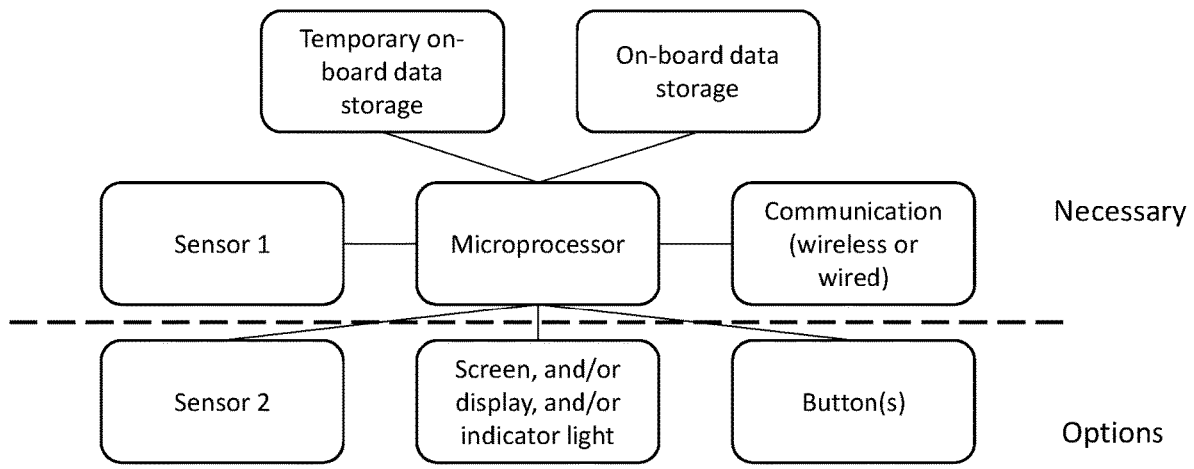
FIG. 5 illustrates the electrical components of the wearable electronic device with possible options.

A preferred wearable electronic device will include a microprocessor within the device. The microprocessor will process the information detected by a motion sensor (e.g., accelerometer), interpret the data, connect with other devices (wired or wirelessly), and communicate processed results to the user directly or through another device, amongst many other functions. (See e.g., FIG. 4.) A microprocessor could also be outside the device but linked to the device for certain remote processing (for example, physically or by means of Bluetooth, Wi-Fi, or some other non-physical means).

A time stamp should be added to the motion sensor data received by the processer. Most microprocessors are capable of performing such function, but others may require the addition of an oscillator (e.g., quartz, oscillator) or some other means of keeping accurate time and adding a time stamp to the data. The term microprocessor and processor have recently come to be used interchangeably. A processor could also be used in place of a microprocessor in this invention.

Figure 3:
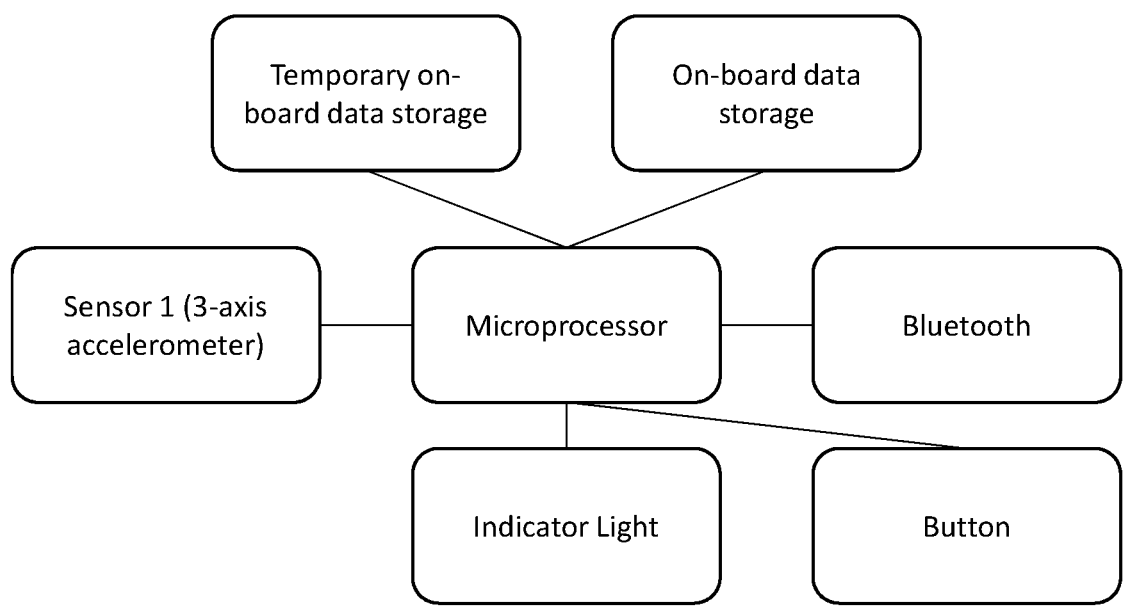
FIG. 3 illustrates the preferred electrical components of an exemplary wearable electronic device.

In a preferred embodiment, the wearable electronic device will also include a means of storing data, although data could be stored elsewhere, such as on another device or in the cloud. In the preferred embodiment, the data storage will comprise two separate data storage devices. One device will be used for temporary storage that will be continually overwritten with new data, and the other data storage will be used to store longer-term information regarding drinking behavior until that data can be sent to a phone, tablet, computer, or other peripheral device. However, the invention described herein may be performed with only one storage location, such as in the wearable electronic device, within the cloud, or on a peripheral device. (See, e.g., FIG. 3 and FIG. 4.)

Figure 2:
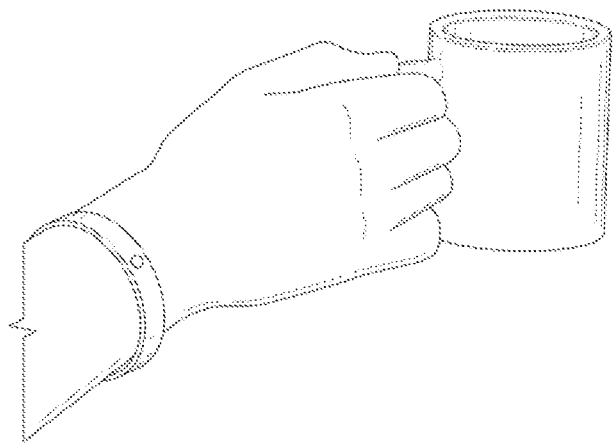
FIG. 2 shows the wearable electronic device of FIG. 1 being worn on a wrist of a user in a preferred location to track consumption processes.

In a preferred embodiment, the wearable electronic device will also include a means of communicating with a phone, tablet, computer, peripheral device, and/or a server. This function can be achieved through a wireless connection such as Wi-Fi or Bluetooth, but can also be a physical connection, including, but not limited to, a USB cable or a ⅛" headphone jack. In its preferred embodiment, the means of communication will be performed using a Bluetooth connection. FIG. 2 shows a preferred embodiment of a wearable electronic device on the wrist of a user holding a drinking apparatus—in this case—a mug.

Figure 10:
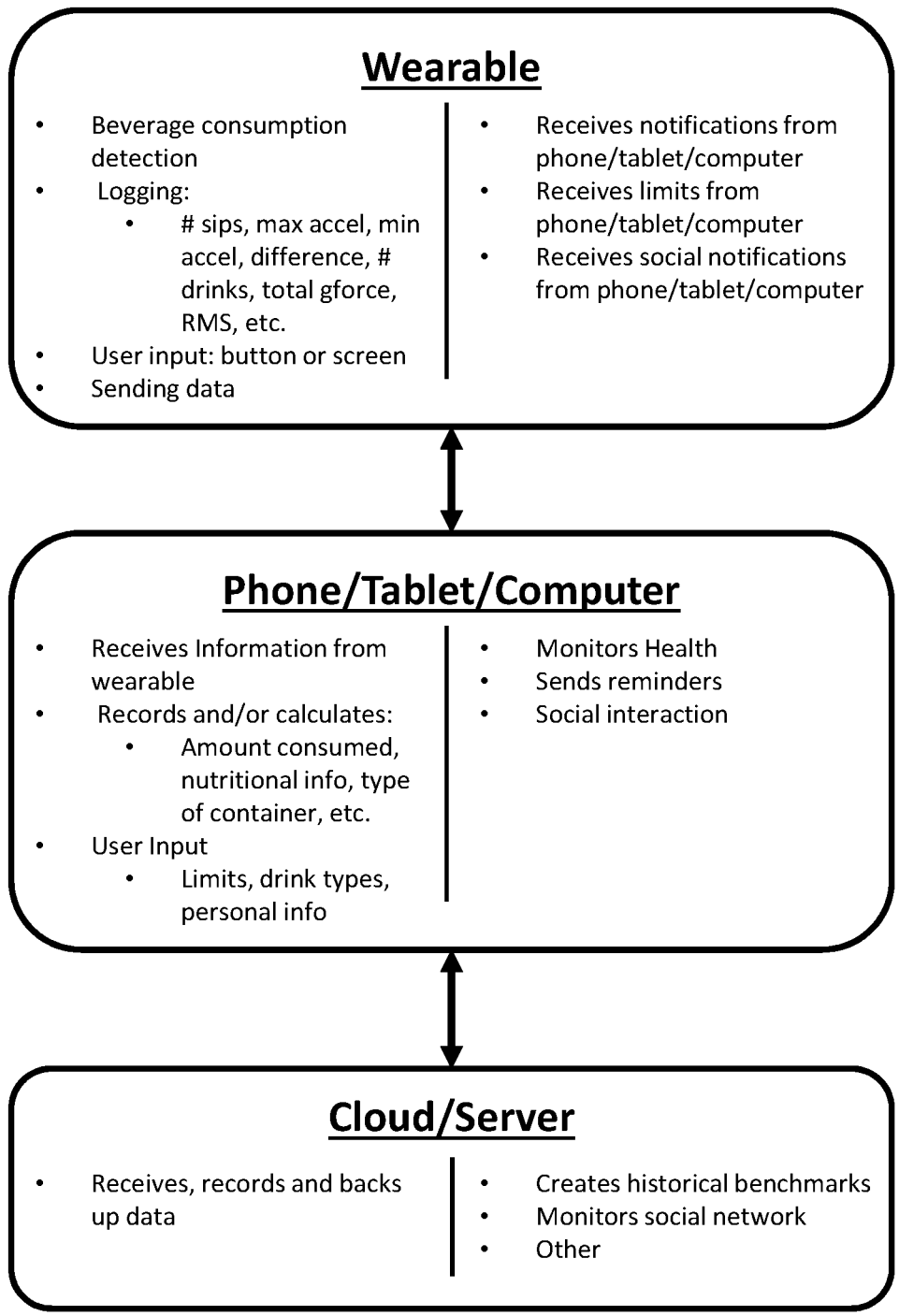
FIG. 10 illustrates the flow of information between the wearable electronic device, a phone/tablet/computer or other external computing device, and a cloud/server.

FIG. 10 shows the flow of information from the wearable electronic device, to a phone, tablet, computer, or other peripheral electronic device, and then from the phone, tablet, computer, or other peripheral electronic device to, in the example, a cloud based server. This flow of information could eventually circumvent the need for a phone, tablet, computer, or other peripheral device if the processing capability and storage capacity of the wearable electronic device increases and/or is able to have an internet or other non-physical connection to a server.

The wearable electronic device will also need to be powered from some power source including but not limited to a battery, solar panel, or any other means for powering the device.

The wearable electronic device may also utilize a button or switch. For example, a single button could be used to turn on the wearable electronic device and allow the user to input necessary information. This could be done by way of one or multiple taps, or holding the button down for a specified period of time. Information can also be entered on the face of the electronic wearable device, or on a peripheral device (e.g., a phone or personal computer) that sends such information to the electronic wearable device. The preferred embodiment of this wearable electronic device will include one button for the user to input information and one switch to power on the device. The preferred location for the switch is in the clasp, which will automatically turn the wearable electronic device on when it is clasped around the user's wrist. This can be done by employing a magnetic clasp, but can also be done through many alternative methods, such as physical means when the band is clasped. A magnetic clasp can be seen in FIG. 1 where when the two ends are attached by means of a magnetic force, a connection or circuit is also completed telling the microprocessor to turn on the wearable device.

The wearable electronic device can also include an indicator light, screen, or display to communicate information to the user. If an interactive touch screen is used, some of the user interface that would normally be performed on a phone, tablet, computer, or other peripheral electronic device can be performed on the interactive screen. This could also take the place of the button or switch as described. The preferred embodiment of the wearable electronic device includes an indicator light (e.g., LED light).

Consumption Detection

Figure 8:
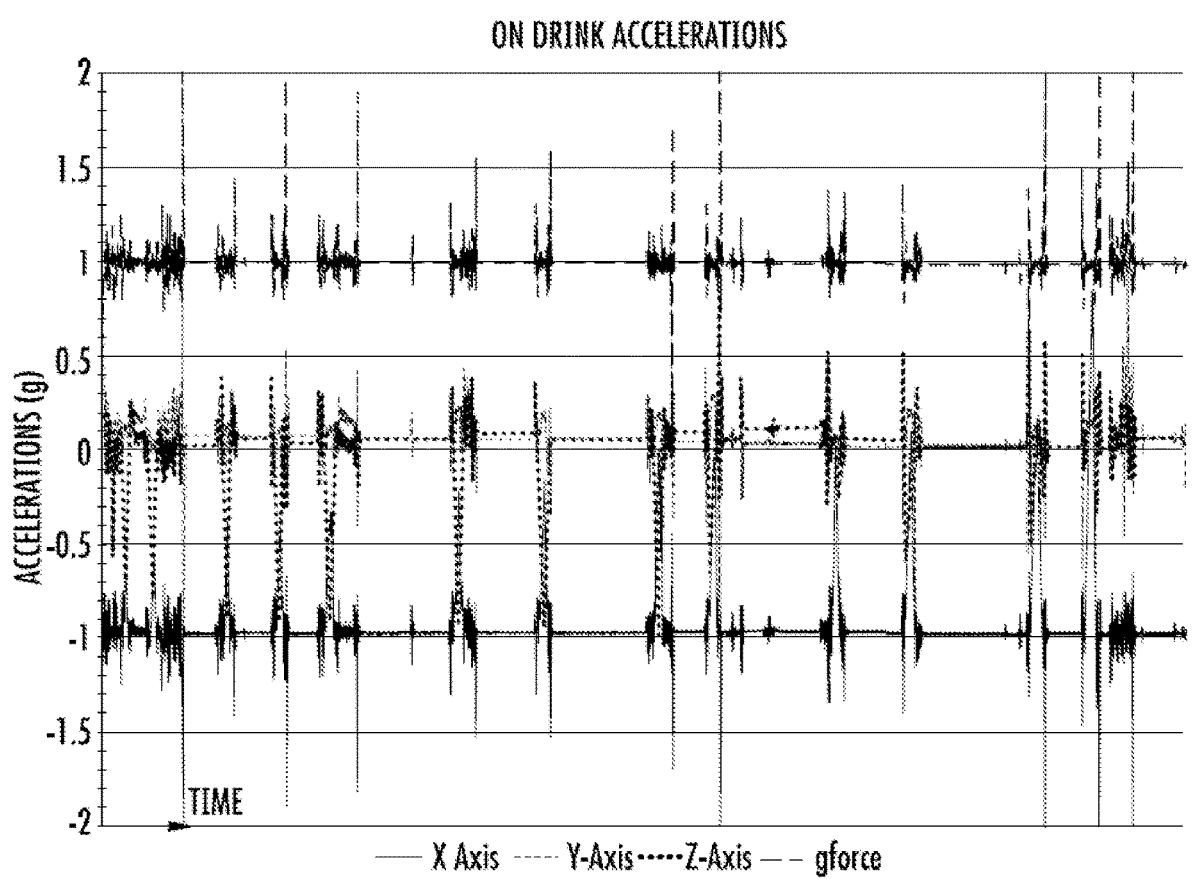
FIG. 8A shows three axis accelerations and the total acceleration when the sensor is placed on the fluid container during the consumption of one entire beverage.
FIG. 8B shows the x axis accelerations when the sensor is placed on the fluid container during the consumption of one entire beverage.
Figure 8:
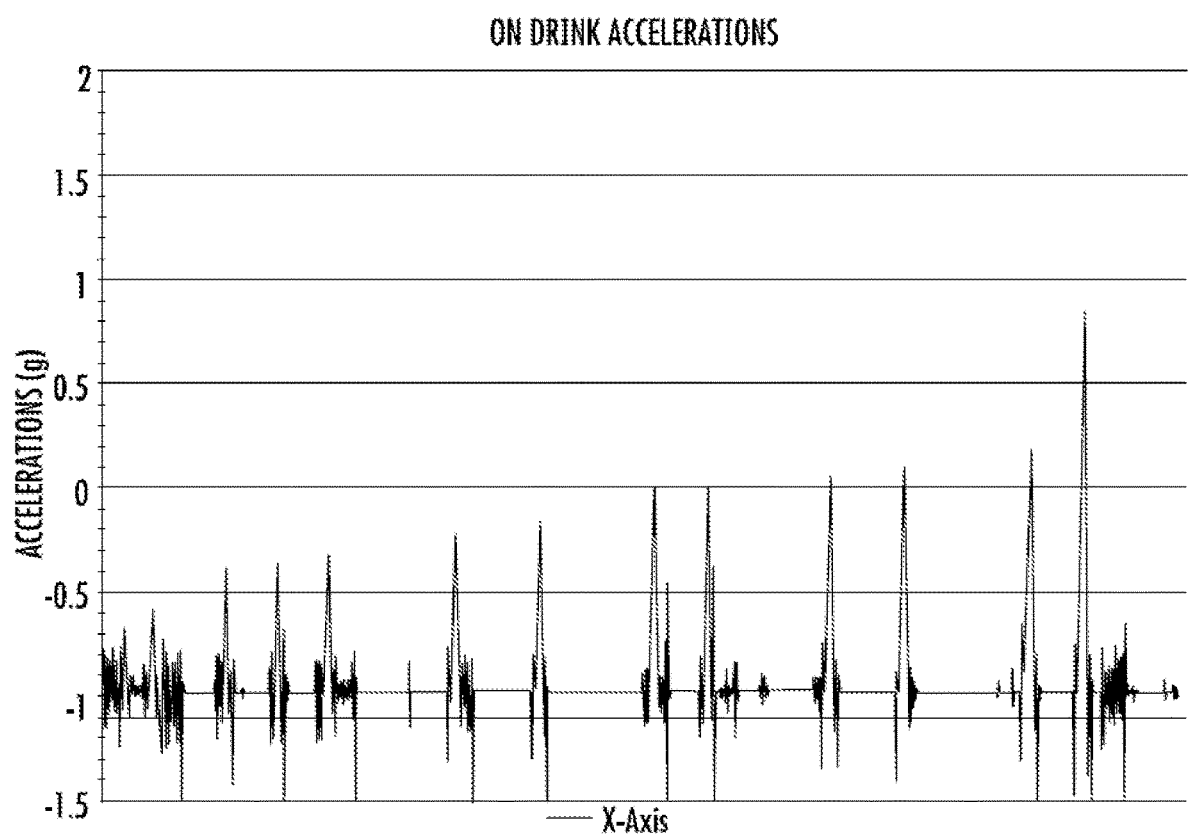

U.S. patent application US 2014/0372045 A1 describes an electronic device with sensors, which fits around a drink container to detect when a sip has occurred and calculate fluid intake by a user. When the sensory band is placed on the liquid container, the specifically-disclosed algorithm detects drinks and sips from monitoring the movement of the container. FIG. 8A shows acceleration data taken from a fluid container during the course of its entire consumption. Because the sensors are on the container, any time a movement is detected it can be assumed that the drink is moving, or changing orientation. This results in a simpler algorithm to differentiate the drinking event from non-drinking events, as opposed to when the sensors are on the wrist as taught by the current invention. The data recorded is also less complex than the data processed according the present invention, because when the fluid container is tilted during consumption, the exact orientation of the fluid container is known based on the alignment of axis with the container itself (See, e.g., FIG. 8B showing only the single x axis measurement.) From this single axis (the x axis shown in FIG. 8a), the tilt of the fluid container can be determined. U.S. patent application 2014/0372045 teaches this calculation in FIG. 11 of that application, and references the following equation:

$$\text{tilt angle} = \arccos\left(\frac{y'}{\text{gravity}}\right) = \arccos\left(\frac{y'}{1}\right)$$

Figure 6:
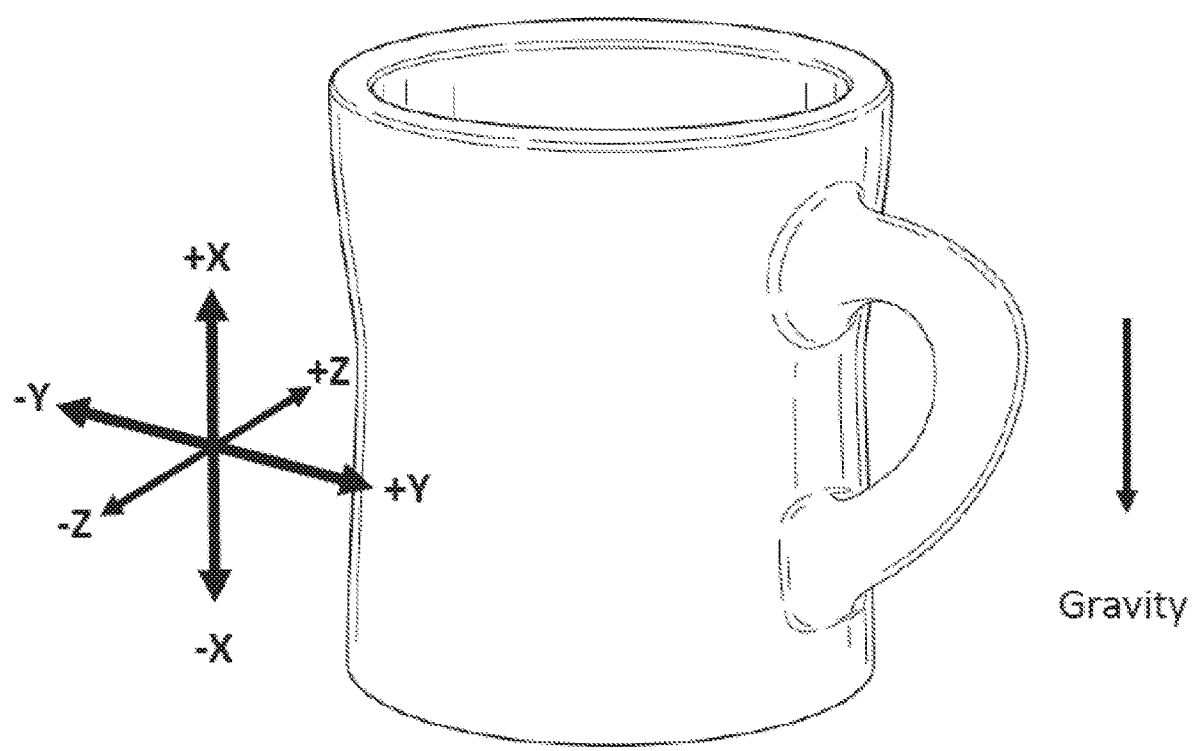
FIG. 6 presents the accelerometer axis orientation and direction of gravitational force for the experiments and data with a sensor mounted on the fluid container.

(See FIG. 6 for axes and gravity in relation to a fluid container.) However, a more accurate manner in which to determine the tilt angle of the fluid container is to first calculate the total accelerations (now referred to as total g below) detected by the fluid container. This total g can be determined by taking the root mean square of accelerations seen on all three axes (the x, y, and z axes):

$$\text{total } g = \sqrt{x^2 + y^2 + z^2}$$

Figure 7:
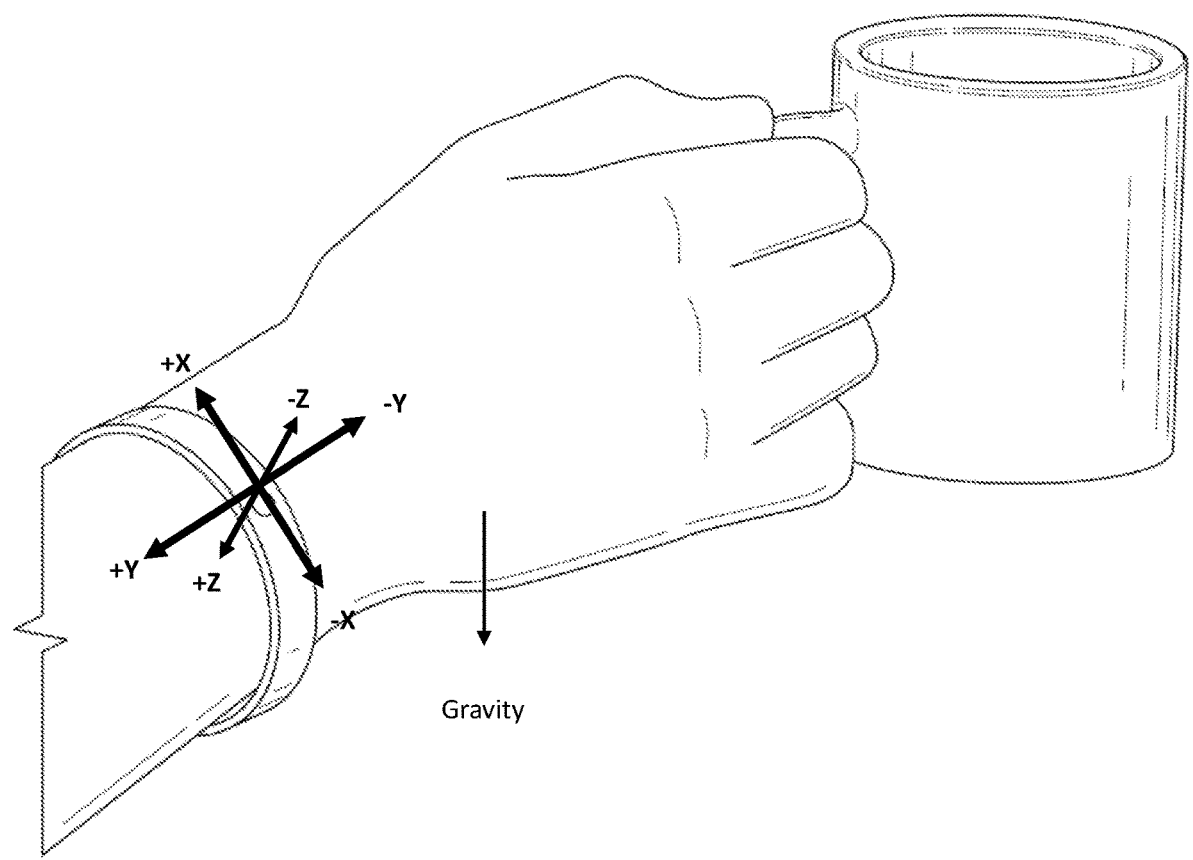
FIG. 7 presents the accelerometer axis orientation and the direction of gravitational force for the experiments and data collected when the sensor is located on a wearable electronic device worn on a wrist.

(See FIG. 7 for axes and gravity in relation to an electronic device as worn on the wrist.) A more accurate tilt angle can then be calculated by factoring in total g instead of gravity as in the equation disclosed in U.S. patent application 2014/0372045. This results in filtering out some accelerations from movements of the fluid container and primarily measuring the gravitational force's effect on the x axis.

U.S. patent application 2014/0372045 detects a drinking event by setting an event threshold. This looks only at the tilt angle of the fluid container (determined by the equation above) and time. Looking at FIG. 8B, an event threshold −0.7 g, where any x axis acceleration greater than the threshold would log a drinking event, all of the drinking events would have been successfully accounted for. If this algorithm were applied to the x axis acceleration data from FIG. 9 (data taken from an on-wrist sensor location during the consumption of a beverage), it would be unable to determine if any drinking events took place due to the varied and more complicated data collected from the wrist of the user.

Figure 9:
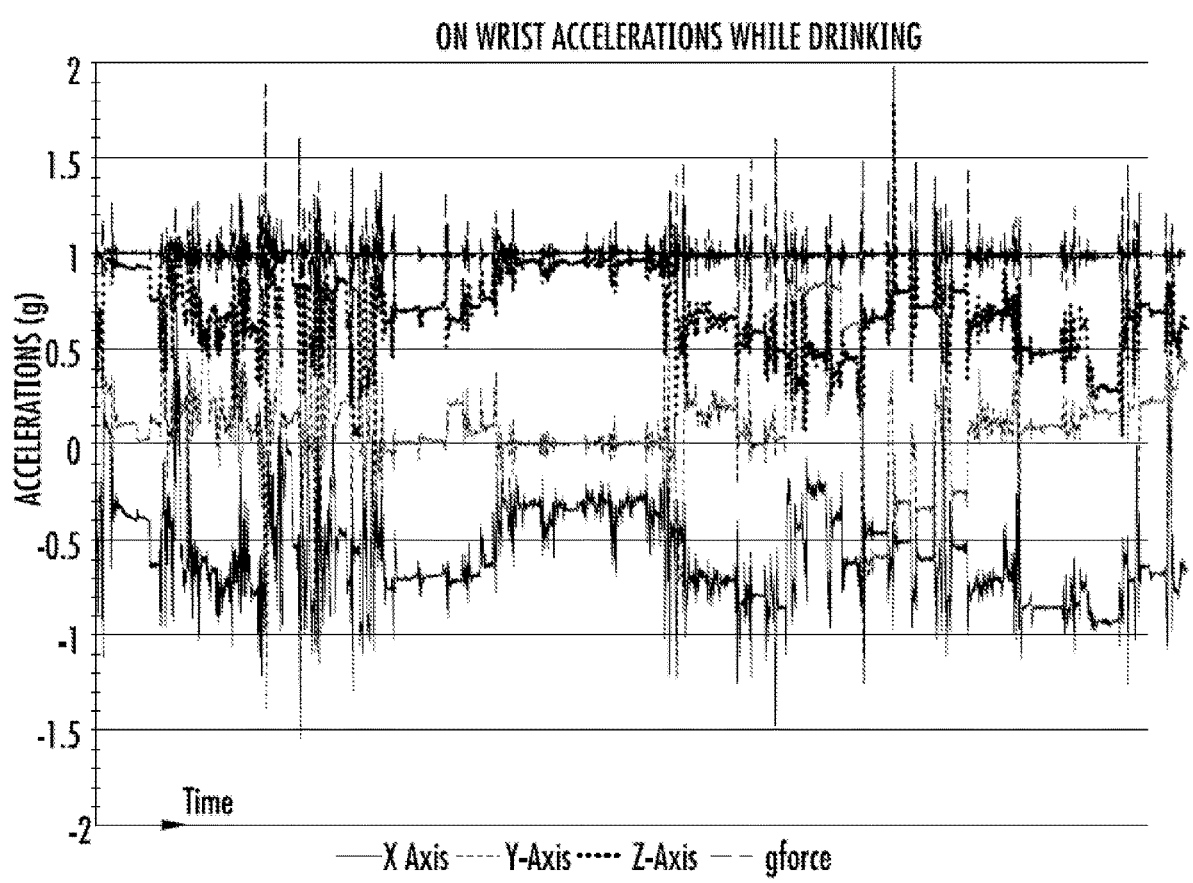
FIG. 9 shows three axis accelerations and total acceleration when the sensor is placed on the wrist of the user during the consumption of one entire beverage.

When the sensor is worn on the wrist as opposed to being placed on the beverage container as taught by U.S. patent application 2014/0372045, the information detected and monitored changes dramatically, making it more complex and therefore more complicated to distinguish drinking events from other non-drinking movements. FIG. 9 shows the accelerations taken from a user's wrist during consumption of a liquid. By a qualitative comparison between FIGS. 8 (on container accelerations) and 9 (on wrist accelerations), the increased difficulty in detecting drinking vs. non-drinking events is represented. The invention described herein solves the problem, allowing for consumption to be accurately detected by a sensor or sensors in a wearable device.

Through extensive data analysis and scientific experimentation, it turns out the consumption processes can be detected and isolated from other movements by measuring accelerations on a user's wrist, hand, finger, or other extremity used to hold and consume liquid, as opposed to requiring the sensor to be placed on the beverage container. In order to accurately determine if a consumption process is taking place, the x, y, and z axes need to be monitored in addition to the total accelerations on the fluid container, which will be referred to as "total g." The total g can be calculated by taking the root mean square of accelerations seen in all three axes:

$$\text{total } g = \sqrt{x^2 + y^2 + z^2}$$

Figure 16:
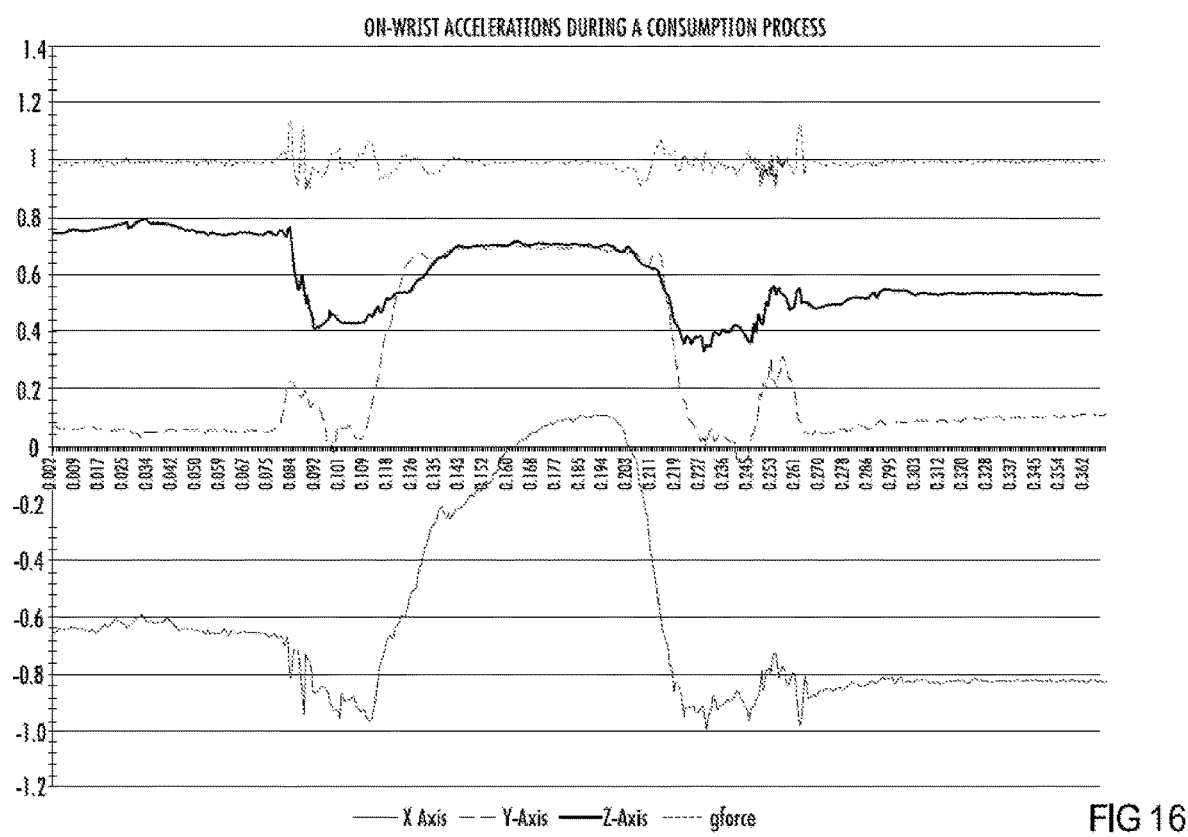
FIG. 16 is a chart showing the accelerations from all three axes along with the total acceleration measured by a sensor worn on a user's wrist during the consumption of liquid from a liquid container.

All four of these accelerations are displayed by FIG. 16 during a single consumption process. In addition to the accelerations in all three axes and the total acceleration, the rotation around certain axes can be used to determine consumption processes. For detecting the consumption process, the most useful rotation to look at is around the y axis, which is parallel to the user's forearm. This is referred to herein as "rotation pitch" and "pitch." The actual angle of the wearable as measured around the user's forearm will be referred to as "pitch angle." All of the rotations can be calculated using the "aerospace rotation sequence" method. To calculate the approximate pitch angle (in radians) around the y axis, the following equation could be used:

$$\text{pitch} = \arctan\left(\frac{x}{\sqrt{y^2 + z^2}}\right)$$

This equation also takes into effect a rotation around the z axis, but because the primary rotation during a consumption process is around the y axis, this equation is used as an appropriate approximation for measuring the pitch.

Figure 15:
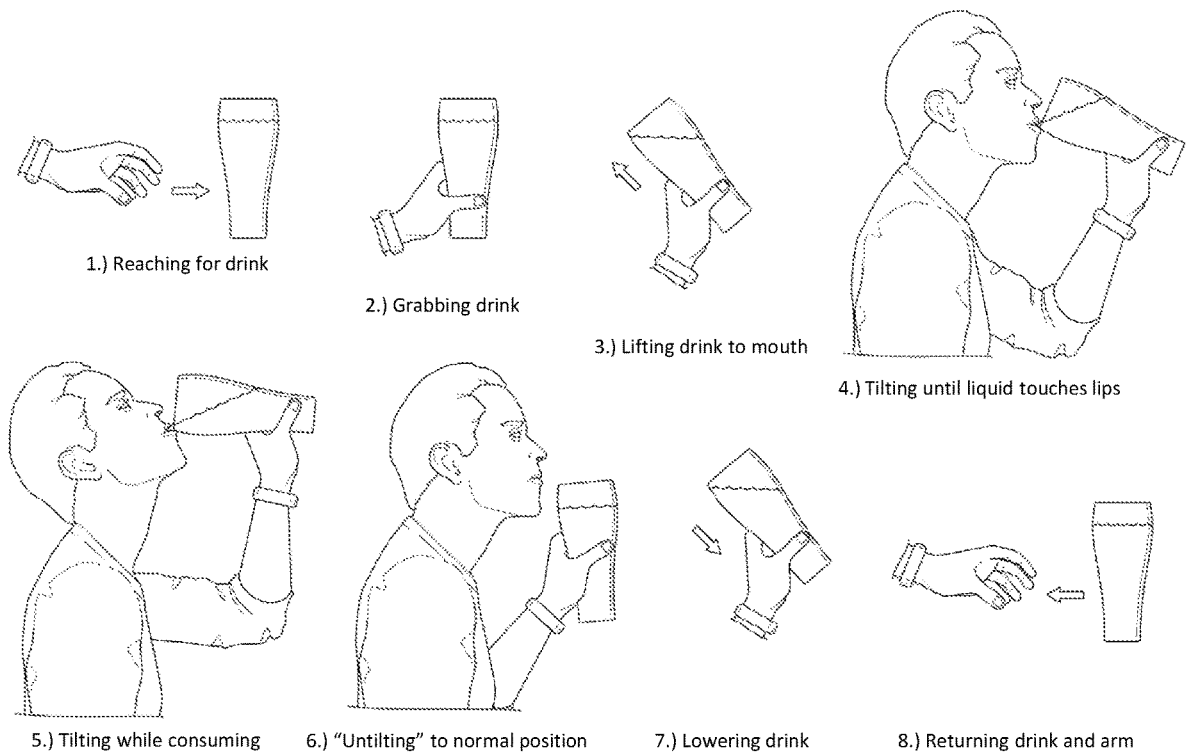
FIG. 15 illustrates eight gestures of drinking that are used, in whole or in part, in an algorithm that detects and measures the user consuming a beverage, as detectable by a wearable electronic device worn on the extremity (e.g., the wrist) used to hold the fluid container.

By analyzing the data of a consumption process, the act of drinking can be separated into eight discrete steps shown in FIG. 15:
1. Reaching for drink;
2. Grabbing drink;
3. Lifting drink to mouth;
4. Tilting until liquid touches lips;
5. Tilting while consuming;
6. "Untilting" (or reversing the drinking tilt) to normal holding position;
7. Lowering drink; and
8. Returning drink and arm.

Figure 17:
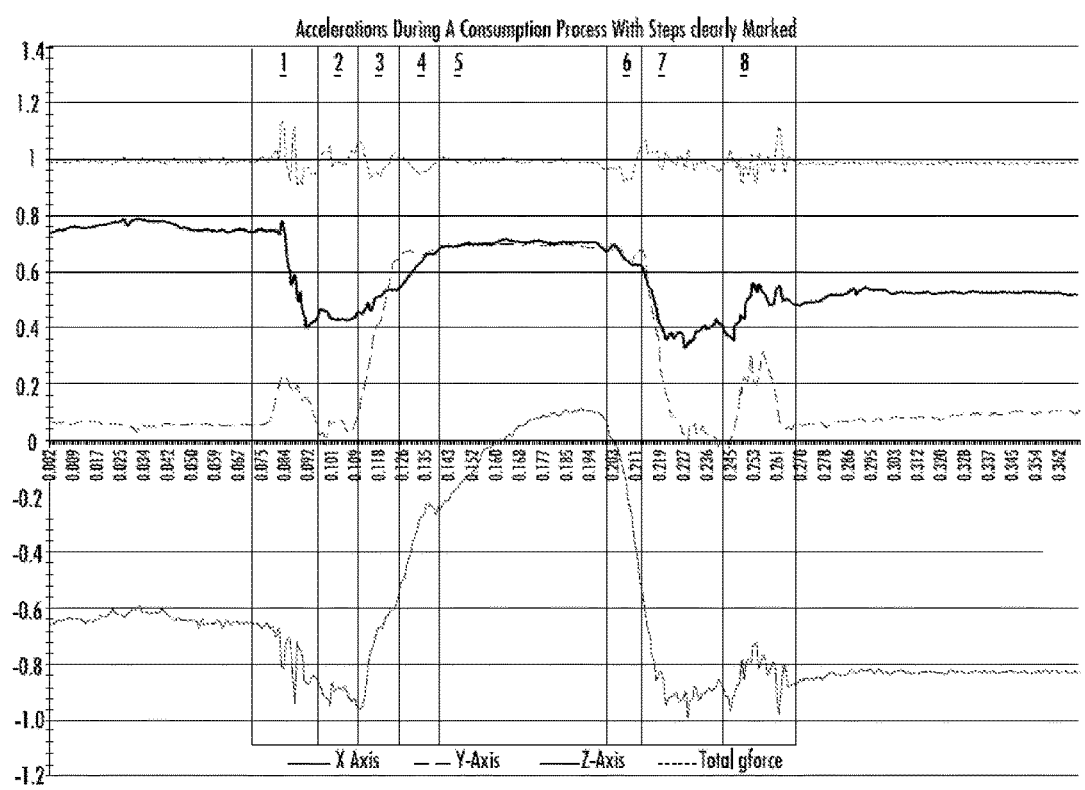
FIG. 17 is the same chart shown in FIG. 16 isolating, in numbered vertical segments, each of the eight steps of consuming a beverage depicted in FIG. 15.

Each of these steps can be detected and measured as information and data as shown in FIGS. 16 and 17. (FIG. 17 shows the same data as in FIG. 16, but each discrete drinking step as numbered in FIG. 15 is overlaid by shaded vertical columns.) Each of the discrete drinking steps and corresponding data from FIG. 17 are explained in detail below:

STEP 1—Reaching for drink: When the user reaches for the fluid container, two distinct motions occur. The user moves his hand and wrist toward the drink container, usually in the y axis, and the user tilts his wrist in order to grab ahold of the fluid container. Both of these actions can clearly be seen in in FIG. 17 at the vertical column numbered 1. The y axis acceleration has an immediate rise and then a subsequent drop that correlates with the total g measured. This indicates a movement of the wrist toward the fluid container. Secondly, the x axis acceleration moves to almost −1 g. This change in x axis acceleration shows the reorientation of the wrist to a more vertical position (along the x axis) in order to grab the fluid container. Note that this reorientation of the wrist an also be seen in the z axis.

STEP 2—Grabbing drink: The act of grabbing the drink can be determined by relatively stable (or flat) readings in all axes (x, y, and z) and the total g with the y axis acceleration close to zero and the x axis acceleration close to −1 g. This signifies that the aria has stopped moving in order to reorient to grab the drink container, but has not yet moved the fluid container closer the mouth of the user. (See column 2 in FIG. 17.)

STEP 3—Lifting drink to mouth: The act of lifting the fluid container to the mouth of the user can be identified primarily by a change in the y axis acceleration measurement, as the forearm is being moved from close to a horizontal position up to an angle that moves the fluid container closer to the user's mouth. When the y axis acceleration levels off, the fluid container can be assumed to be positioned near the user's mouth. It is also important to recognize that the x axis and z axis accelerations are also rising as the wrist is beginning to tilt the fluid container. The movement of the wrist and fluid container will be measured by a quick fluctuation in the total g to both greater than and less than 1 g (starting the movement and stopping the movement). An approximate range for this fluctuation will be between 0.9 g and 1.1 g. (See column 3 in FIG. 17).

STEP 4—Tilting until liquid touches lips: During this step, the container is already positioned at the user's mouth, meaning the y axis acceleration is relatively steady as shown in column 4 of FIG. 17. The x axis and z axis accelerations continue to climb as the user moves his wrist and arm to allow the liquid to touch his lips. When liquid is touching the lips, the user changes his movement during consumption. This is shown in the data by a leveling off of the z axis and slight dip in the x axis as depicted in column 4 of FIG. 17. The user usually has a quick pause at this moment before starting the consumption phase. This movement and pause is seen in the total g with a slight dip and return to 1 g. This marks when the liquid is touching the user's lips.

STEP 5—Tilting while consuming: This step marks the actual consumption of the fluid. Most notably, the y axis and z axis accelerations remain steady and relatively flat during this step, in addition to almost no changes in total g. The only sip that sometimes sees a drop in both y and z axis accelerations is the last sip (and potentially second-to-last sip). This is due to a change in the movement (raising the elbow higher than normal) compared to all other periods of consumption. Depending on how the user is holding the fluid container, the y and z accelerations can be different, but they will be steady. During the movements before and after the consumption phase, the movements in the wrist will be logged by the total g, but during consumption, this is stable and measures almost 1 g, the gravitational force. During all of this, the x axis acceleration continues to climb as liquid is being consumed and eventually levels off as the consumption of liquid slows and eventually stops. (See column 5 of FIG. 17.)

STEP 6—"Untilting" to normal holding position: The "untilting" phase marks the end of consumption and return of the hand, wrist, and fluid container to a normal upright position. This can be seen in the data by a reduction in the x axis acceleration and the start of a reduction in the z axis acceleration. During this phase, the y axis measurements are mostly constant. As the "untilting" motion begins, the total g will start to change, registering motion compared to the relatively steady consumption step. (See column 6 of FIG. 17.)

STEP 7—Lowering drink: The lowering of the fluid container can be detected by rapid decrease in the x axis and y axis accelerations as the wrist returns to the mostly vertical position holding the fluid container in an upright manner and the forearm moves from an inclined to a mostly horizontal position. As the x Axis decreases to almost −1 g, it tends to stabilize and stay near −1 g as the drink is still being held. The z axis is relatively steady during this phase. (See column 7 of FIG. 17.)

STEP 8—Returning drink and arm: This step is comprised of moving the fluid container to its final position, releasing the container, and moving of the user's arm to a non-drinking position or natural state. This step can be determined by a sudden rise and fall in the y axis acceleration and a change in the x axis acceleration once the drink has been released. Small changes in the total g register the movement of this step. The z axis is measuring a portion of the movement and rotation of the forearm. (See column 8 of FIG. 17.)

It is noteworthy that moving the sensor location from one wrist or hand to the other (for example moving it from a user's right wrist to his left wrist) will affect the y axis measurements. In FIG. 17, the y axis acceleration measurements move from about 0 g to 0.7 g during Step 3. If the sensor were to be worn on the other hand or wrist, the y axis measurements would show the same movement, but in the opposite direction. Lifting of the forearm would move measurements from about 0 g to −0.7 g in this example.

While all of the aforementioned steps together make up the motions and movements detectable by a normal or full consumption process, some of these steps might not occur if the way in which the user is consuming the beverage changes. For example, these steps require the fluid container to be sitting down on something such as a table or bar, before the process begins. The sensors and processor then register the movement to pick up, consume the liquid, and return the fluid container to a seated position. If the user decides to hold the fluid container alongside his body between sips or the actual consumption of the beverage in step 5, steps 1, 2, and 8 will be eliminated. If the user decides to hold the fluid container at his lips in-between two consecutive sips, steps 1, 2, 3, 7, and 8 will be eliminated. The algorithm disclosed herein is able to adjust for changes in drinking behavior. For example, even if behavior changes, the algorithm still detects which steps have been performed, allowing general tracking of the position of the fluid container and a corresponding starting point for another sip. Consequently, even as drinking behavior changes, overall drinking behavior can be analyzed because all 8 steps are not necessary to detect and monitor the consumption phase.

The sip detection algorithm relies on the gestures based around eight steps of the consumption process. Of the steps listed in FIG. 15, steps 4, 5, and 6 will almost always be present when a sip is being taken. Sometimes steps 3 and 4 will appear to be combined into one step as will steps 6 and 7. Steps 1, 2, 3, 7, and 8 serve to further help detect when a sip is being taken and classify if the liquid container has been set down, held in a hand, and other important consumption behaviors.

It is important to be able to distinctly determine step 5 because this portion of the consumption process contains information about the user's drinking behavior, such as the peak x axis acceleration during the sip, the consumption duration, the rate at which the liquid container is being tilted, along with other information.

The information entering any of the algorithms used, including but not limited to the sip detection algorithm, the final sip algorithm, and the container and drink recognition algorithm, can be in the form of raw data from the motion sensor(s) or could be preprocessed in any form. An example of this would be if the pitch angle were calculated and then used in any respective algorithm. For example, during most consumption processes, the calculated pitch angle will actually mirror the x axis accelerations very closely, but can enhance certain movements which will make detecting the individual steps of the consumption process more accurate. When the y and z axis acceleration measurements are steady, which is common for almost all consumption processes, there is little difference between the calculated pitch angle and the x axis acceleration. However, during the last consumption process of a beverage, the y and z axis accelerations tend to move closer to 0 g throughout Step 5. This movement dramatically increases the calculated pitch angle, making it easier to detect the final sip of a beverage.

Figure 11:
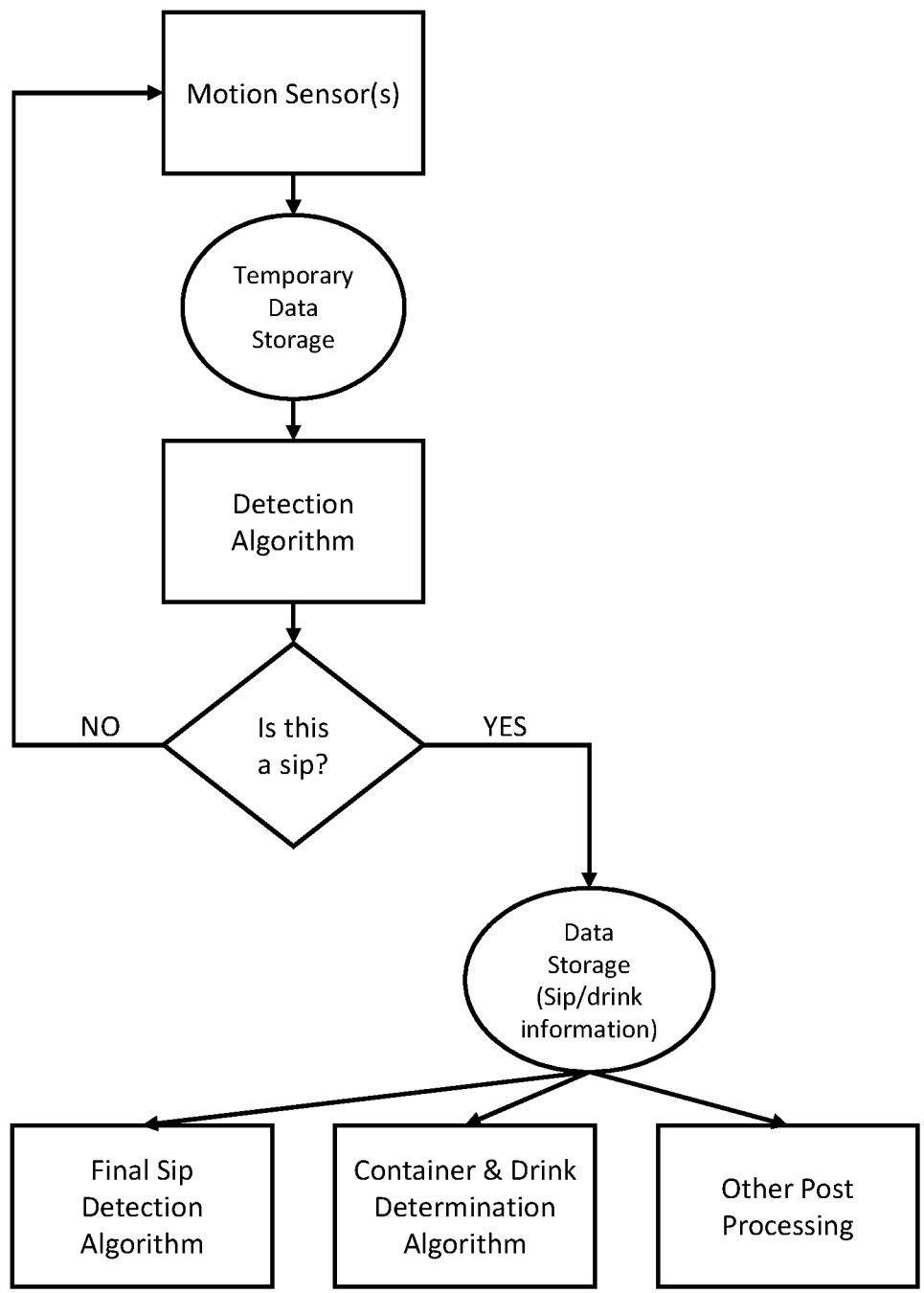
FIG. 11 is a flowchart representing what occurs when a consumption process is detected or when a false or non-event is detected, and the related processing information.

As explained above, the act of consuming a beverage has multiple stages before the actual consumption takes place, but can also start and end on different steps throughout the process. Consuming may include, but is not limited to, any one or more of reaching, lifting, drinking, tilting, untilting, ingesting, consuming, grabbing, and/or lowering. Detecting when a sip is occurring before it has occurred is relatively difficult, but detecting the sip after the event has occurred becomes easier to recognize as the event has more data points to analyze. For this reason, the sip detection algorithm uses a temporary data storage that will continually record the accelerometer's data for a set period of time. The set period of time should be, for example, set to 10 seconds in order to detect most consumption processes of average duration, but can be as short or long as desired. Setting a period of time closer to 60 seconds will enable detection of longer than average duration consumption processes, such as consuming an entire beverage in one drinking motion. Doing so will require more storage and processing capacity for longer temporary storage. The temporary storage will continually be overwritten but will give the sip detection algorithm enough time to access past data to be able to recognize the drinking gestures outlined above. FIG. 11 shows this process. Once a sip is detected, the necessary and important information from that sip will be logged and recorded in the more permanent data storage. Relevant information includes but is not limited to peak x axis acceleration, Step 5 duration, duration of full consumption process, time between sips, position of drink after consumption, full data from the consumption phase (Step 5), and full data from the entire consumption process once it has been isolated. This more permanent data storage will keep the information on the wearable electronic device until the information has been sent to a phone, tablet, computer, peripheral device, or server. Once this has been completed, the information can be deleted from the wearable electronic device to free up space for more data collection.

Logging and storing the information above tracks the drinking behavior of the user over time in addition to improving the tracking and detection during the consumption of a single beverage. One application of this is that by knowing the position of the beverage (whether it has been set down or is currently being held), the algorithm can adjust and look for the consumption process to start on the appropriate step of the consumption process. This can be seen applied to a detection algorithm in FIG. 21A. For example, if a user picks up his drink and returns it to the table for the first sip, picks up his drink and holds it by his side for his second sip, and then returns the container to the table after his third sip, and so on, storing this information will allow the processer to keep tracking and analyzing the consumption of the entire beverage over time by helping with detection.

While FIG. 11 depicts a preferred embodiment of information flow to detect and analyze a consumption process with the temporary storage, it is possible to create a detection strategy without the temporary storage. For example, the sip detection algorithm may only measure the first four steps to detect a sip is about to take place before logging the data on the data storage during Step 5.

Figure 21:
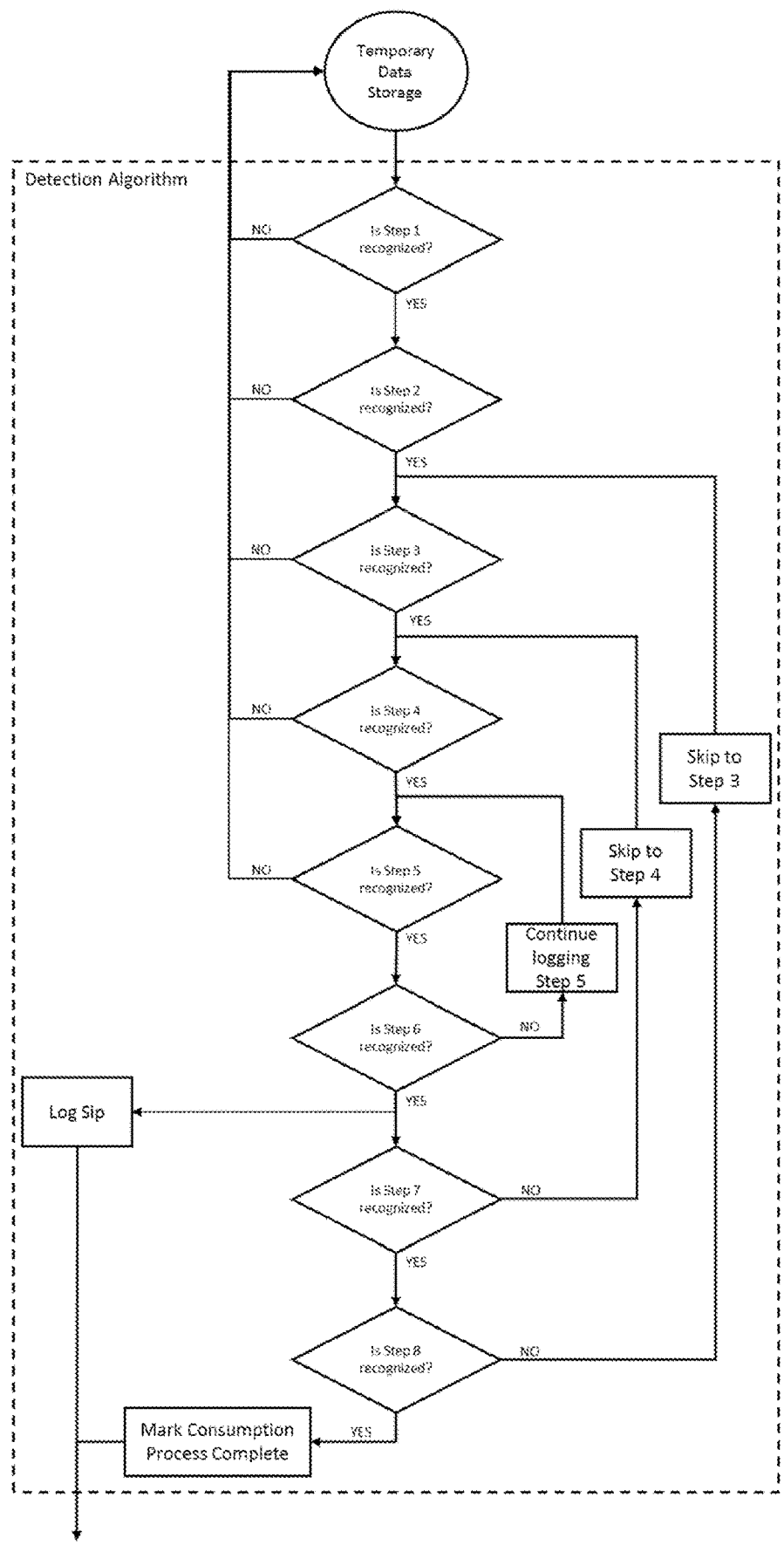
FIG. 21A is a flowchart illustrating a sip detection algorithm that includes all eight steps of the consumption process shown in FIG. 15.
FIG. 21B is a flowchart illustrating a simplified sip detection algorithm.
FIG. 21C is a flowchart illustrating a simplified sip detection algorithm that also includes the ability to determine the location of the fluid container.
Figure 21:
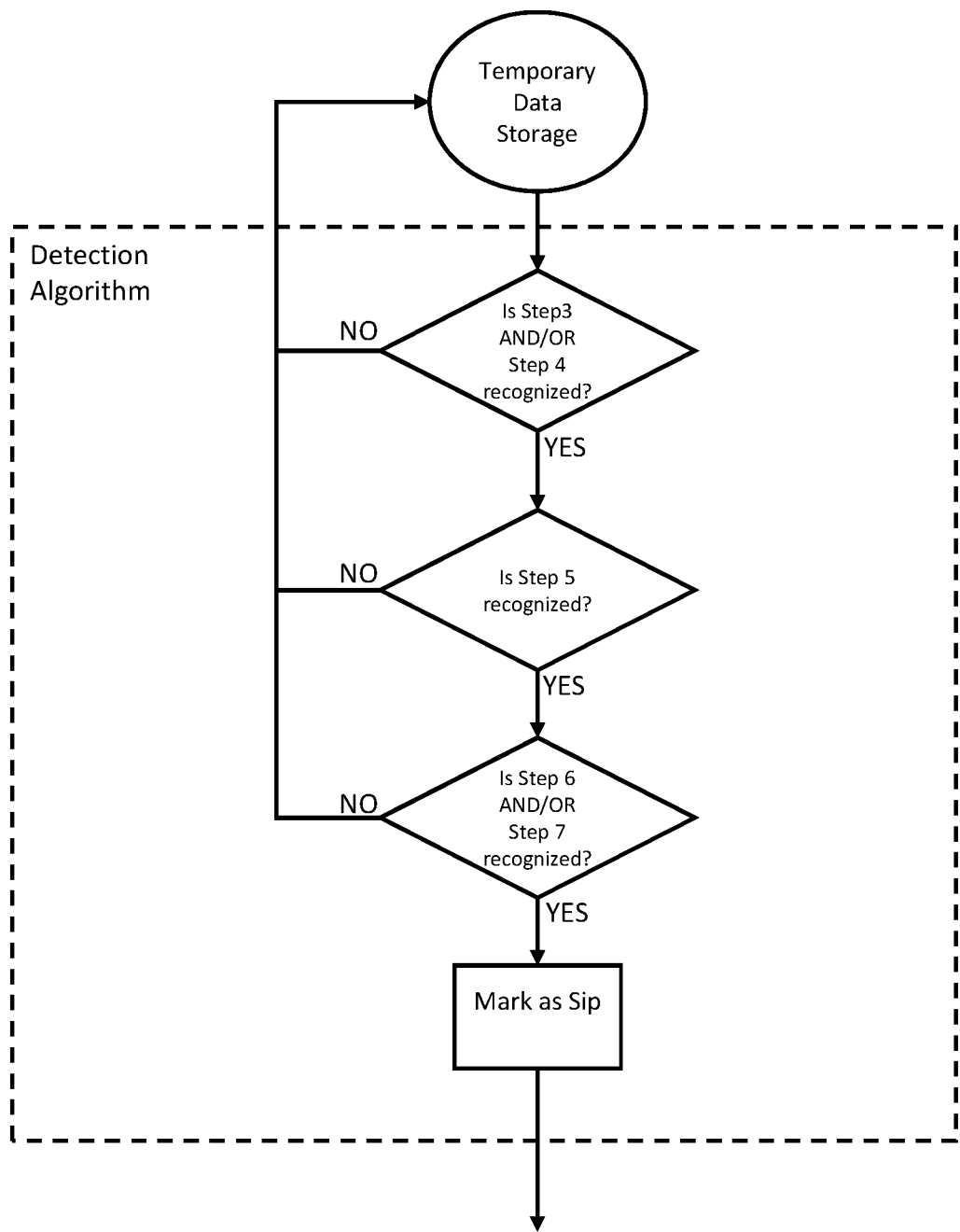
Figure 21:
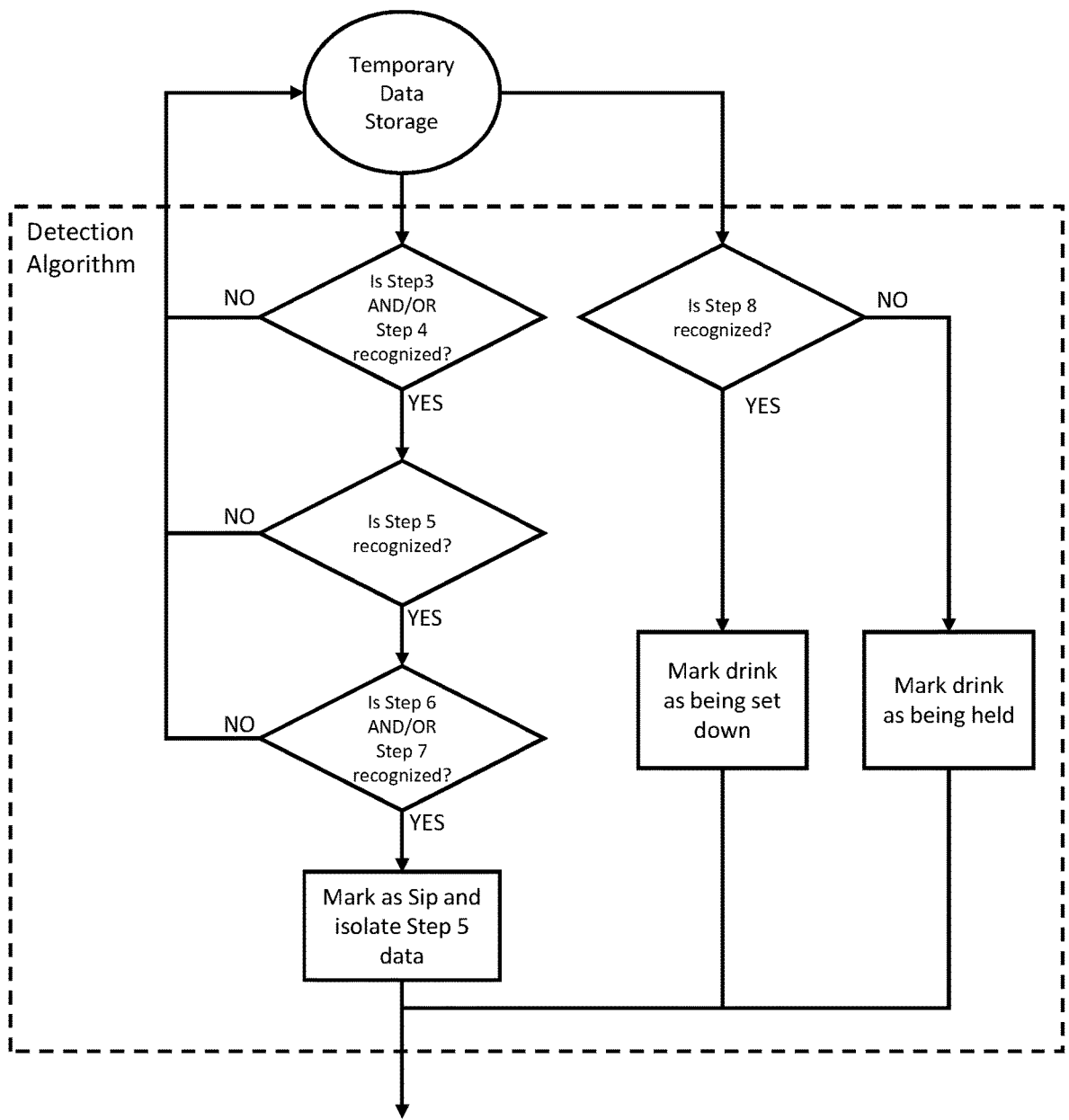

A few examples of sip detection algorithms are provided in FIGS. 21A, 21B, and 21C. FIG. 21A shows a detection algorithm using the detection of the eight steps of the consumption process in a linear progression in order to determine if a sip was taken and which step to anticipate next. The benefit of this process is that it tracks if the drink has been set down or not, and the algorithm can predict which step to look for next when detecting a sip.

FIG. 21B show an algorithm that negates the need to track each individual step of the consumption process. A critical part of a detection algorithm is to recognize and isolate Step 5, the consumption phase. The consumption phase will be located between Step 4 and Step 6 of the consumption process. Most times, Steps 3 and 4 are combined into one fluid movement by the user, and similarly, Steps 6 and 7 are also combined into one fluid movement. The algorithm in FIG. 21B looks specifically at Steps 3 and 4, Step 5, and Steps 6 and 7 as three distinct portions marking the preparation, the consumption, and the conclusion.

The algorithm in FIG. 21C combines the simplicity of the detection algorithm in FIG. 21B with also being able to track the location of the beverage container. By having a parallel decision path looking for Step 8 recognition, the algorithm can determine if the user is continuing to hold the container in a hand or if he has returned the container to a separate resting location.

Both raw, preprocessed, and post-processed data can be used to recognize the individual steps. Step 5 is the most significant step to be able to recognize. This step is recognized by comparing the overall movement of a person's wrist, hand, finger, or extremity to the actual position and orientation of said wrist, hand, finger, or extremity. During Step 5, the total g is steady and nearly equal to 1, the gravitational force. This phenomena by itself means that the user is not moving the extremity with which the sensor is located. But during Step 5, there is a steady and resizable change in the x axis measurements. The angular pitch can also be used instead of the raw x axis measurements. Such a change while the total movement is stable is very uncommon in movements other than drinking and can be used to detect Step 5, the consumption phase. Analyzing the position of the extremity through the y and z axis accelerations in addition to looking for the steps of the consumption process before and after Step 5 increase the effectiveness of the detection algorithm.

Figure 18:
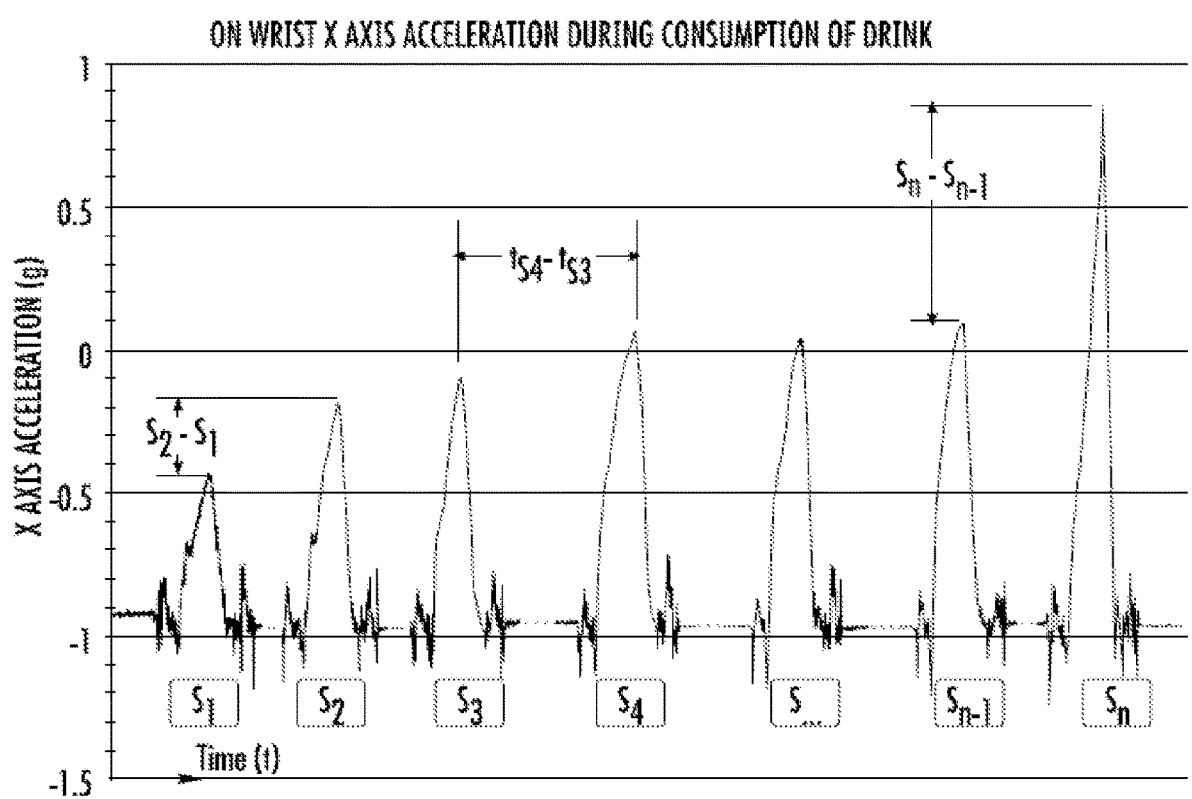
FIG. 18 is a chart displaying the on wrist x axis accelerations during the consumption of one entire beverage, from a first sip $S_1$ to a last sip $S_n$.

FIG. 18 shows different x axis accelerations throughout the consumption of liquid in a container. The accelerations from the first sip to the last sip will change in magnitude, but their relative characteristics should remain the same. Analyzing this information allows for determination of a consumption process ranging from a full fluid container to an empty fluid container. For example, accelerations are different from a full container when compared to an empty container. This difference allows for tracking how much fluid is being consumed over time. Tracking the duration of step 5 over time can also determine the amount of fluid being consumed. Combining these approaches of tracking number of sips, duration of the consumption phase (Step 5), and other critical data increases the accuracy of determining the amount of fluid consumption.

While the accelerations referenced in the above description provide enough information to recognize consumption processes, there are other ways to analyze the data in order to isolate the consumption process. For example, measuring the frequency and magnitudes of the oscillations in the total g allow for the characterization and determination of each drinking step. Additionally, taking the Root Mean Square for only two of the axes allows for certain gesture recognition. Calculating other information based on the acceleration data, such as taking a derivative or integrating to respectively determine the change in acceleration (also known as jerk) or velocity also increases accuracy. Multiple derivatives or integrals can be calculated to determine jounce, position, or other information. A calculation for measuring the revolution around an axis was presented earlier for one axis, but this can be performed for all axes using the three-axis acceleration data. The addition of a three-axis gyroscope is one way to overcome potential regions of error. Based on the data from the 3-axis accelerometer, many more analyses can be conducted to help isolate steps of the consumption process.

Last Sip Detection

Detecting the final sip of a drink is an especially critical data point to collect in logging and tracking the amount of fluid consumed. Several means for detecting the last sip are taught herein. FIG. 18, for example, shows the x axis accelerations with a sensor on a wrist throughout the consumption of an entire beverage. Peak x axis accelerations of consumption processes tend to rise gradually throughout the consumption of a beverage. This graph also shows that while the peak acceleration tends to rise, it can level off for a few sips or even decline if the beverage is not being tilted as far back from sip-to-sip. A consistency, however, is that the last sip or those shortly before the last sip show large differences in peak accelerations compared to the previous sips. This phenomenon is due to the user attempting to get all of the fluid out of the container.

Figure 12:
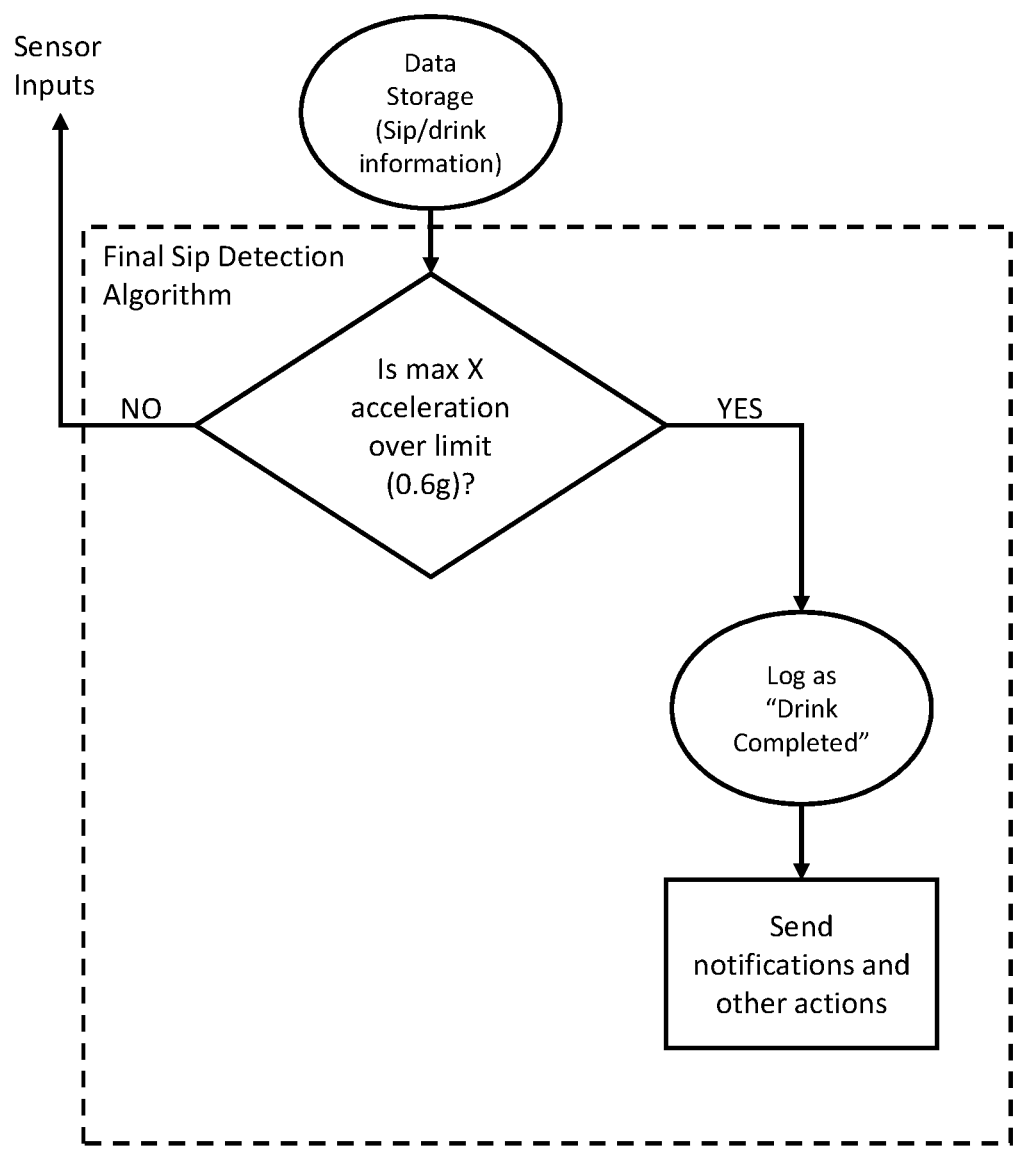
FIG. 12A is a flowchart showing steps in determining and detecting whether a final sip has occurred.
FIG. 12B is a flowchart showing steps in determining and detecting whether a final sip has occurred.
Figure 12:
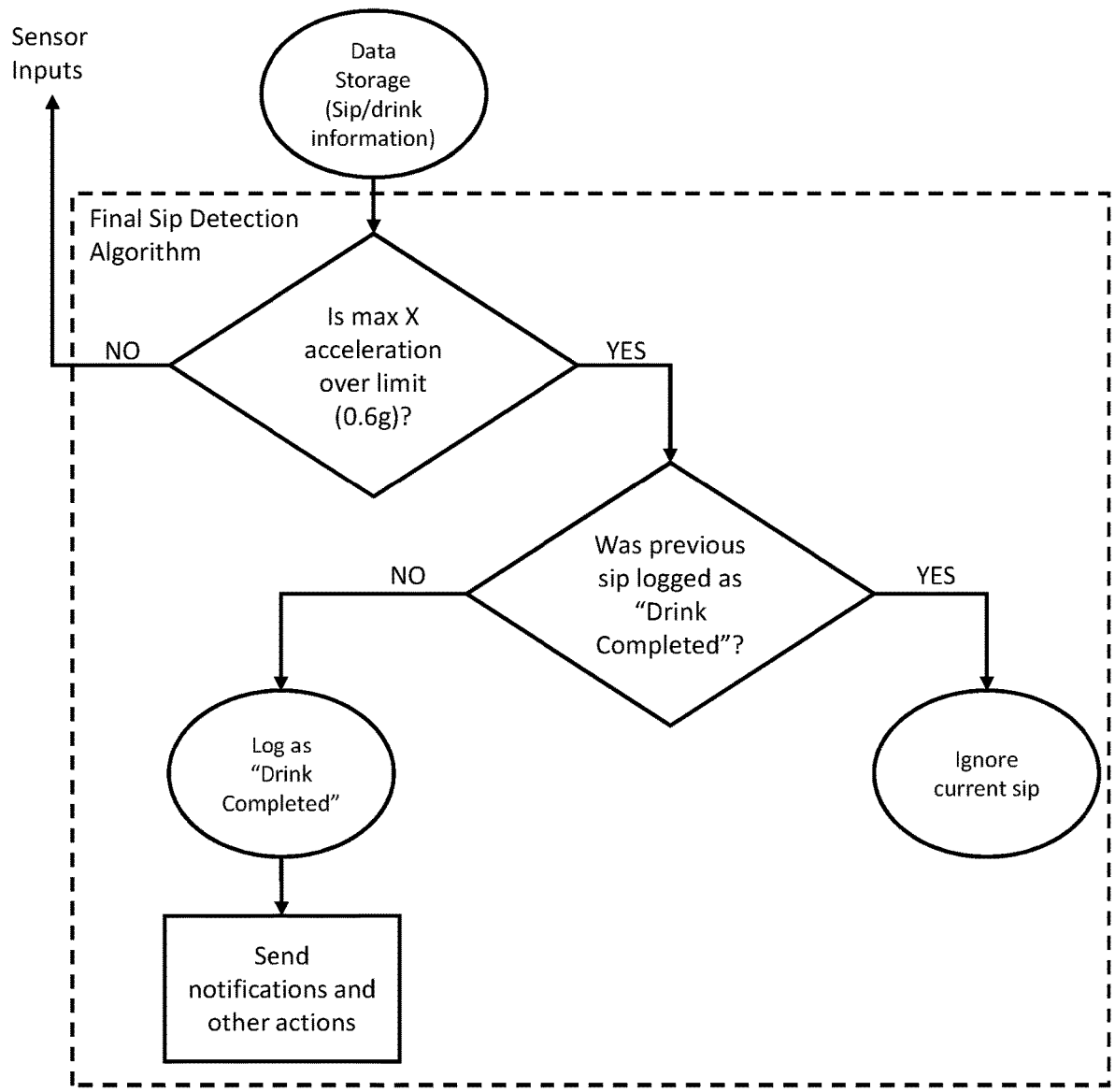

FIG. 12A illustrates one way of determining the final sip, by measuring only the accelerations of the x axis. From the data collected with a sensor on the wrist, the average peak x axis acceleration of a last sip across all different fluid container types is 0.76 g with a 0.1 g standard deviation and ranging from approximately 0.63 g to 0.95 g. The difference between the second-to-last and final sip averages to 0.45 g with a 0.1 g standard deviation. Lastly the second-to-last sip averages to 0.3 g with a standard deviation of 0.19 g and ranging from 0 g to 0.5 g. Looking at the large discrepancy between the second-to-last sip and the final sip, setting a limit or threshold on the x axis for determining a final sip, is an accurate means of detecting a final sip. A threshold could be, for example, 0.6 g and could range from 0.5 g to 0.9 g. An issue with determining the final sip by using only a threshold occurs when the user will take a "second final sip." This occurs when the user takes a final sip, but thinks there might be a few more drops in the fluid container. If the user were to want to consume those final drops, he might take a second sip that registers a peak x axis acceleration within the "final sip" threshold.

A solution to this problem is to add a second aspect to the flowchart as seen in FIG. 12B. This aspect effectively asks the question whether the previous sip was logged as "Drink Completed," which will allow the final sip algorithm to accurately log one drink for each one actually consumed. There is the possibility that if the user were extremely quenched for thirst, they might consume two full containers of liquid in only two very large sips. If this were the case, the data for Step 5 would be extremely longer than normal with a slow rise in the x axis acceleration until it reaches its peak. This anomalous consumption process can be identified and marked in accordance and therefore not ignored by what is seen in FIG. 12B. Once again, the drinking steps taught herein allow for detection and analysis of many different types of fluid consumption and behaviors, even if they change during consumption of one beverage or from one beverage to another.

Figure 13:
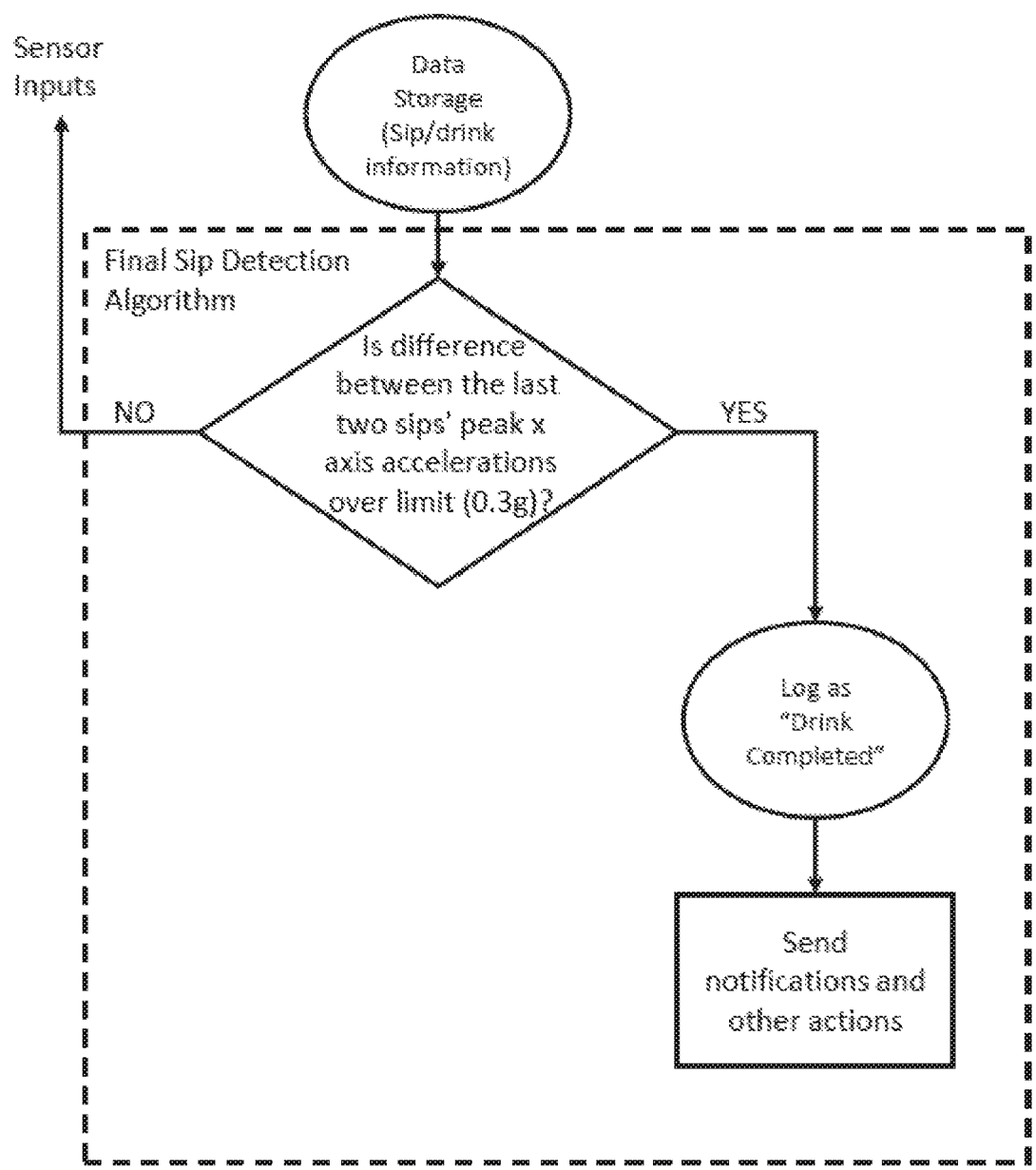
FIG. 13 is a flowchart showing steps in determining and detecting whether a final sip has occurred.

FIG. 13 shows another possible way of determining the last sip by measuring the difference between the second-to-last sip and the final sip. As stated above, the difference between the second-to-last and final sip averages, in this example, to 0.45 g with a 0.1 g standard deviation. The average difference between all other sips throughout the consumption of a drink averages to 0.04 g with a standard deviation of 0.1 g and a maximum difference of 0.26 g. The smallest difference between the second-to-last and final sip measured was 0.35 g. Without any overlap between 0.26 g and 0.35 g, the final sip can be determined by calculating the difference between sequential sips.

A third possible way of determining the last sip is by measuring the difference between the last sip and the first sip. This is a feasible way of logging the last sip and a completed drink, but it relies on starting a new drink with a first sip. To improve this technique, a timer could be employed that considers the end of a drink (sip or entire container) after a specified time period.

Figure 14:
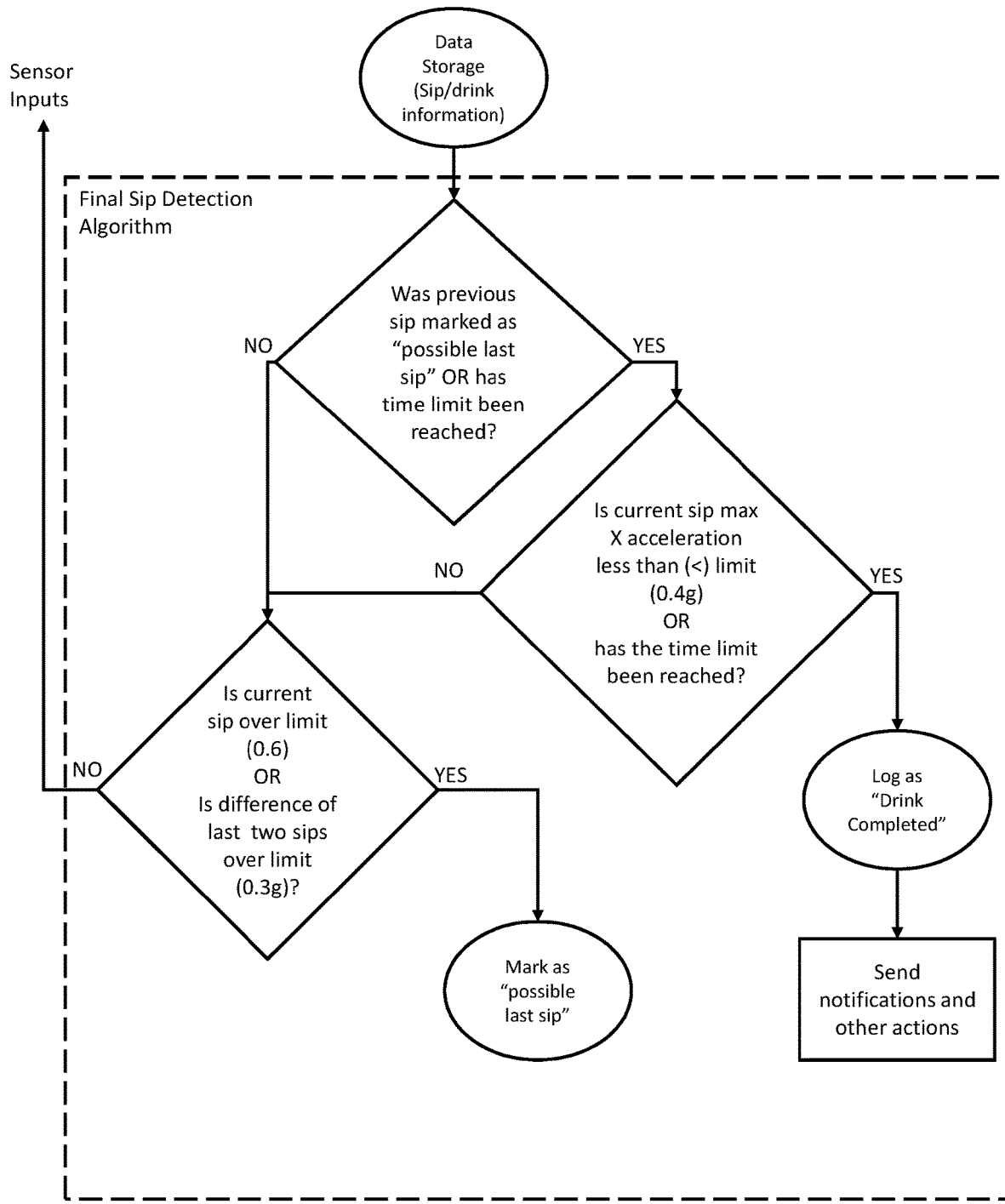
FIG. 14 is a flowchart showing an embodiment of steps in determining and detecting whether a final sip has occurred.

A fourth possible way of determining the last sip of liquid from a container is exemplified in FIG. 14. This method combines two of the previously disclosed methods and identifies possible last sips. If a maximum x axis acceleration is over a specified limit, such as 0.6 g, that sip will be marked as a possible last sip. Similarly, if the difference between sips is over a threshold, such as 0.3 g, that sip can also be marked as a possible last sip. This fourth method of determining the last sip differs in that a sip is only marked as "possible last sip," whereas the other methods definitively identify a final sip. If the user starts another drink, the max x axis acceleration will be below a threshold, such as 0.4 g, identifying the start of a new drink. At this point, the previous last sip will mark the end of a drink and the proper notifications and actions will take place. Similarly, if a certain time limit is reached after a sip is marked as "possible last sip," that sip will mark the completion of a drink. Starting another drink or having sufficient time elapse would confirm that the "possible last sip" was indeed a last sip of the beverage container.

Figure 22:
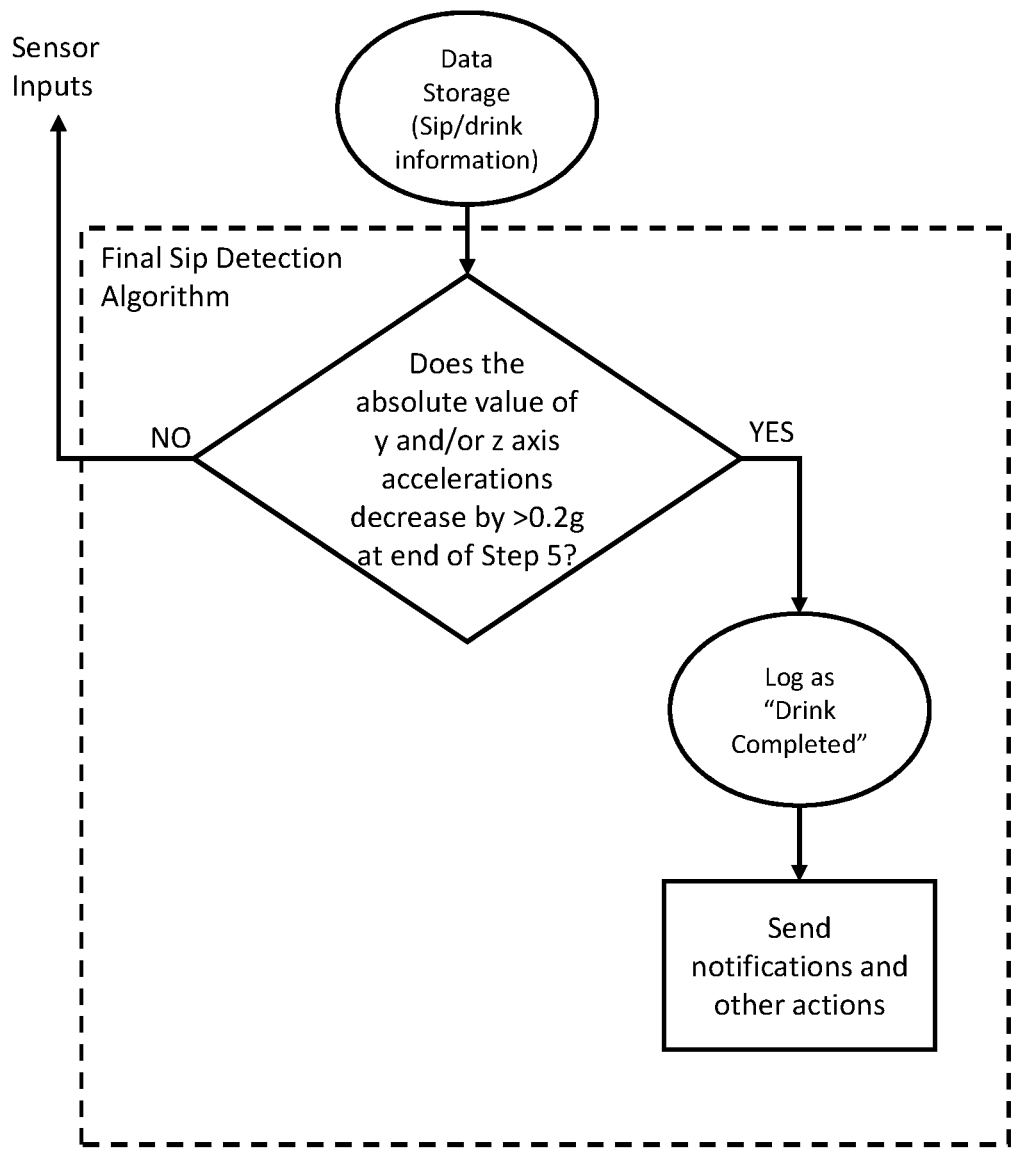
FIG. 22 is a flowchart illustrating a final sip detection algorithm primarily concerned with y and z axis accelerations during Step 5.

A fifth way of determining the last sip is by analyzing the y and z axis accelerations during step 5. In almost all of the previous sips, the y and z axis accelerations level off and stay relatively consistent throughout the consumption phase, step 5. The last sip, and sometimes second-to-last sip, are the only ones that register a change in the y and z axis accelerations. They tend to decrease as the x axis acceleration is continuing to increase. This is attributed to a change in the user's elbow position during consumption in an attempt to tip the liquid container in a more vertical position. The final sip algorithm could be set to log a sip as a last sip if the y and/or z axis accelerations decrease by more than 0.2 g throughout step 5. This algorithm is shown in FIG. 22.

The methods above describe different approaches of determining the last sip based on data from an accelerometer on a wrist and corresponding limits and thresholds. These methods can be adapted for use with an accelerometer placed on the actual beverage container in order to determine when a drink or container of liquid has been completely consumed. Different limits and thresholds would need to be used based on corresponding data for the technique, but would follow the reasoning explained herein. For example, when the sensor is on the fluid container, primarily the x axis accelerations matter. With this sensor location, the method of determining a last sip shown in FIG. 13 is a relevant algorithm to use. The limit used for an on-wrist sensor is 0.3 g and this limit will also work well for an on-drink sensor location. If the method of determining a last sip shown in FIG. 12A or 12B were to be used, the limit would have to be decreased to 0.2 g from 0.6 g shown in FIG. 12A or 12B. The problem with this method is that overlap exists depending on what type of fluid container is used. A solution to this potential problem is a more complex algorithm, like that shown in FIG. 14, which should be used with the new on-drink sensor limit of 0.2 g.

If a user is drinking from multiple containers, for example, both water (from a glass) and coffee (from a mug) with consumption processes overlapping in time period, say during the same meal, one way of solving this particular quandary vis-à-vis the invention taught herein is as follows. In most situations similar to this, one of the multiple drinks consumed is likely to be water. For this reason, an example of a solution is to have a button (or some other means of signification) on the wearable electronic device which can be used to log when a sip is water and when it is not. This way, the wearable electronic device will still be able to track the consumption of the other non-water drink, while also keeping a better log of the user's water intake. This method can apply to any situation in which there is a primary drink and a secondary drink. In the previous example, water was the secondary drink, but the user decides which drink is primary and which drink is secondary.

With a system similar to this, data about each sip and consumption process will be stored, and the sips from a secondary drink (e.g., water, soda, etc.) will be marked or flagged as secondary. This will allow certain algorithms using this data to ignore the secondary sips and focus on the primary sips. An example of this is with the container and drink recognition algorithm. If this algorithm is processing necessary information (e.g., peak x axis accelerations, pitch angle, etc.) from a series of sips in which some have been from a secondary drink, the algorithm will be able to remove the sips marked secondary, and focus on the sips marked primary to determine the type of container the beverage is being consumed from or the actual beverage itself. Similarly, a system like this can be used for the final sip detection algorithm, properly knowing when the primary or secondary drink has been completed.

Conversely, if this algorithm is processing necessary information peak x axis accelerations, pitch angle, etc.) from a series of sips in which some have been from a secondary drink, the algorithm will be able to remove the sips marked primary, and focus on the sips marked secondary to determine the type of container the secondary beverage is being consumed from or the actual beverage itself. While the example in this case uses one button, the device itself could have multiple buttons to mark a second beverage, third beverage, fourth beverage, and so on, if the user decides to have multiple beverages.

Sometimes drinks are being constantly refilled. Both water and coffee are examples of this phenomenon when consuming these beverages at a restaurant, for example. In these situations, when a last sip cannot be detected, a difference in peak x axis accelerations can detect and register a refill. Consequently, total amount consumed may be calculated by the duration of Step 5 from the data and other learned averages of the user (i.e., how much liquid the user typically consumes in one sip).

In interpreting and analyzing the raw or preprocessed data in any of the algorithms used, the magnitude of data, duration of events, frequency of events, time or distance between events, and other characteristics from the motion sensors are critical in determining necessary information, including but not limited to if the consumption process has occurred, the amount of liquid consumed, the type of liquid container, and the type of liquid being consumed.

Container Recognition

Recognizing the type of container from which the liquid is being consumed (e.g., open-top glass, mug, bottle, aluminum can, stemmed-wine glass, etc.) helps to also recognize the type of liquid being consumed. Whereas most diet/fitness trackers require the user to input when the user consumed a beverage, how much was consumed, and the type of beverage—and U.S. patent application 2014/0372045A1 requires the user to enter the size and type of container the liquid is contained in—the current invention can determine not only when a liquid is being consumed, but also the type of container from which it is being consumed.

Figure 20:
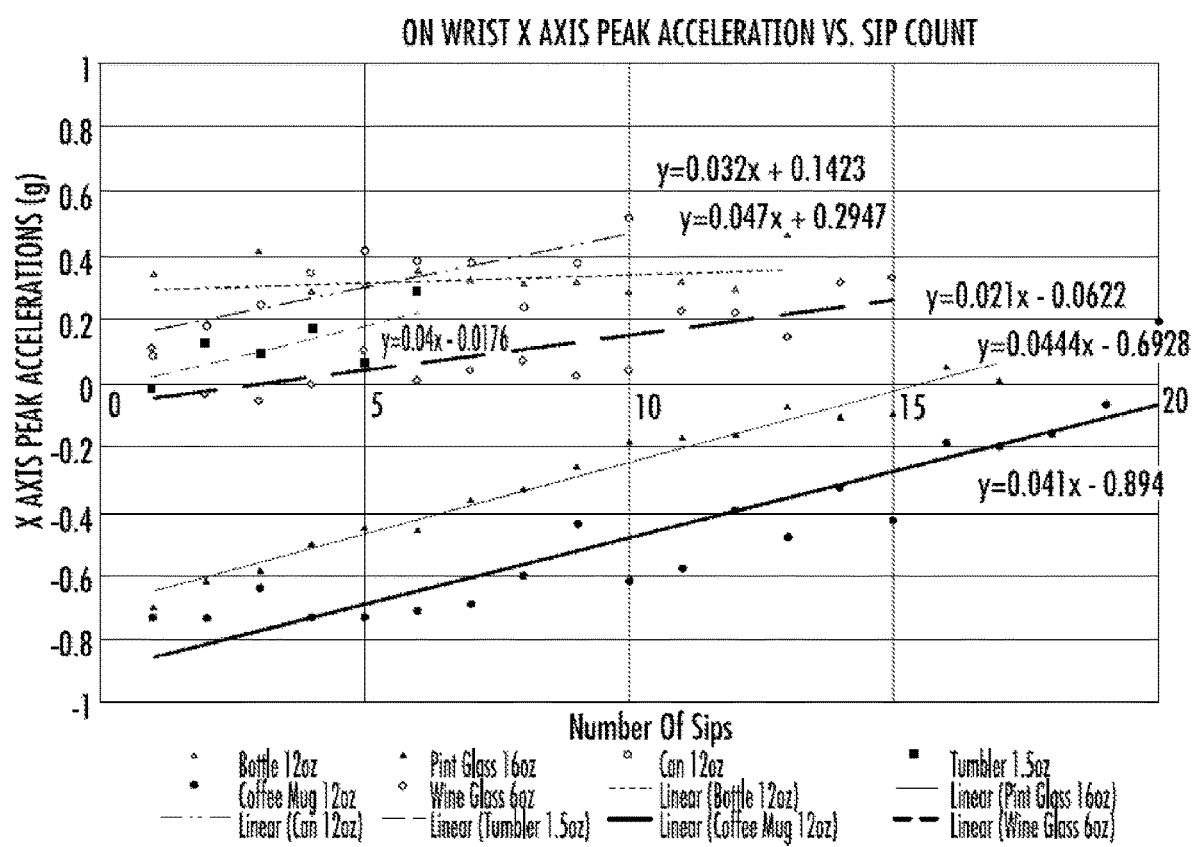
FIG. 20 is a chart plotting the peak x axis acceleration from an on-wrist sensor during each consumption process throughout the consumption of a beverage. Varying types of liquid containers are compared against each other, and trend lines show the linear regression results for each container type.

This method of container recognition is based on scientific research finding that each type of glass or other type of container has a unique pattern when plotting and/or regressing the peak x axis acceleration on either the time or number of sips taken throughout the consumption of a beverage. In FIG. 18, for example, the peak x axis acceleration for each individual sip is shown to be gradually rising throughout the consumption of the beverage when looking at the overall trend. FIG. 18 shows this trend when the sensor is placed on the wrist of a user, but a similar trend is also present when the sensor is on the drink. The last sip has a significantly higher peak x axis acceleration than the prior sips. The peak x axis acceleration is found during Step 5 of the eight steps of drinking seen in FIG. 15 and corresponding FIG. 17. The first sip peak x axis acceleration, last sip peak x axis acceleration, and all peak x axis accelerations from sips between the first and last sips have unique values based on the type of container from which the liquid is being consumed. Data from an experiment is plotted in FIG. 20 showing the peak acceleration for each sip throughout the consumption of a drink (excluding the last sip) for different types of fluid containers with an on-wrist sensor location. Similar trends can be seen when the sensor is placed on the drink itself when regressing the x axis peak accelerations on time or the number of sips.

Figure 19:
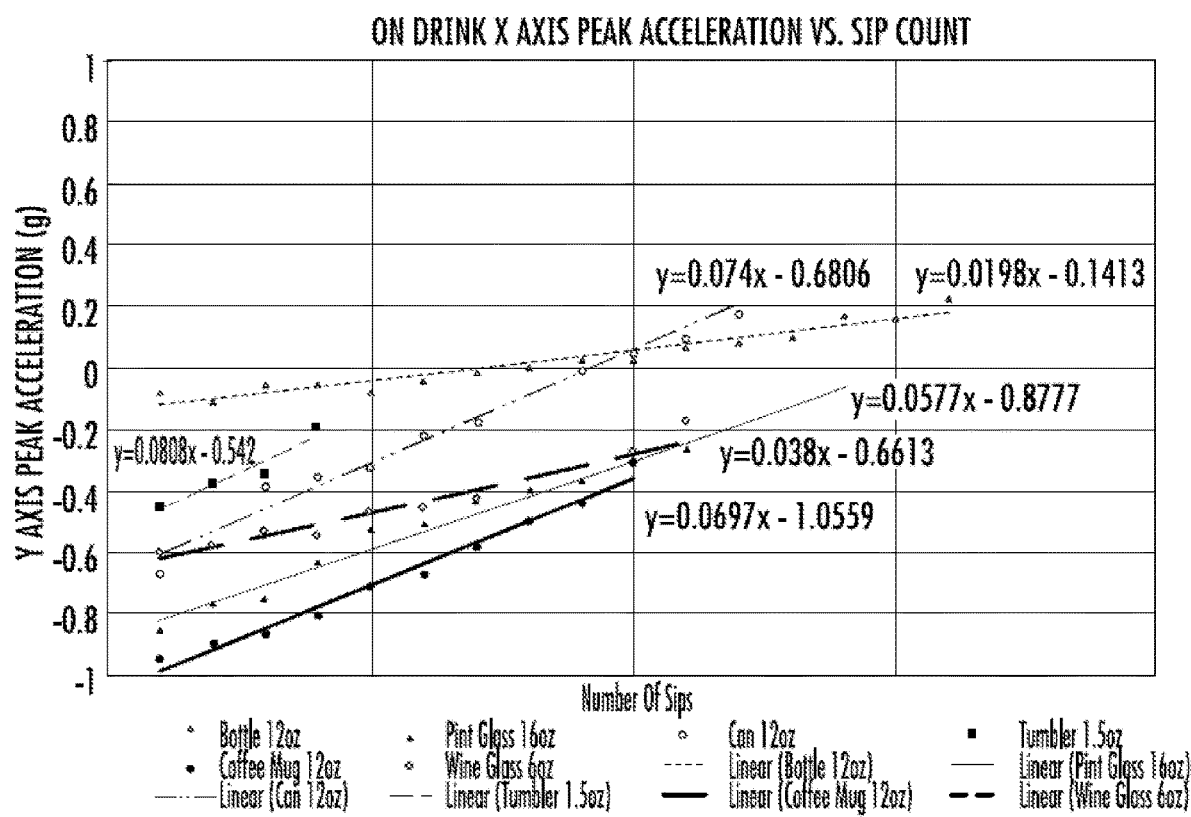
FIG. 19 is a chart plotting the peak x axis acceleration from an on-drink sensor during each consumption process throughout the consumption of a beverage. Varying types of liquid containers are compared against each other, and trend lines show the linear regression results for each container type.

FIG. 19 shows peak x axis accelerations from a sensor placed on the drink plotted against the number of sips throughout the consumption of a beverage, taken from six unique and common types of beverage containers. If using this method to recognize the type of container the liquid is being consumed from, it is a preferred embodiment to factor in sips $S_1$ to $S_{n-1}$. Because the last sip $S_n$ usually has a much higher peak acceleration, it skews the results, affecting the ability to most accurately categorize the type of beverage container from which the liquid is being consumed through a linear regression. Other types of analysis are capable of determining more complex trends that can allow the last sip ($S_n$) to be included in said analysis. A linear regression is also depicted between the peak accelerations and the number of sips from each container type. The results of the regression are shown as a trend line on the chart in addition to the equation. Looking at the six different containers, each type has a unique starting point, unique ending point, and unique slope. For example, fully filled open top containers such as a pint glass or coffee mug have significantly lower first sip peak accelerations when compared to a container with a constrained opening such as a glass bottle or aluminum can. A partially filled open top container such as a wine glass or tumbler glass containing liquor tends to demonstrate first sip peak accelerations between a fully filled open top container and a container with a strained opening such as a glass bottle.

FIG. 20 shows similar data to that of FIG. 19, but with an on-wrist sensor location instead of a sensor placed on the beverage container. The containers on both charts include a 12 oz. glass bottle, a 16 oz. pint glass, a 12 oz. aluminum can, a tumbler or low ball glass containing 1.5 oz, of liquor, a 12 oz. coffee mug, and a standard stemmed wine glass containing 6 oz. of wine, although this method of determining container type can be applied to any liquid container.

By comparing the real-time data being collected by the wearable electronic device to the known trends of different types of containers, the invention can determine the type of container from which a liquid is being consumed. The regression analysis determines the type of container, but it is not necessary since other techniques exist as described herein. For example, knowing the average difference of peak accelerations between each sip and the peak acceleration of the first sip is enough to reasonably classify the type of container being used. Through machine learning, the wearable electronic device and/or program on a phone, tablet, computer, other peripheral device, or server can learn the habits of each user and provide more accurate results over time based on the user's inputs and selection/correction of fluid container types.

Based on knowing the type and size of container, the wearable electronic device or the program on the phone, tablet, other peripheral device, or computer will be able to recognize or recommend the type of drink being consumed, making it easier for the user to actually log the drink consumed. It is also possible to narrow the selection of possible drinks being consumed in a similar manner to what is described for the container type. For example, a hot tea or hot coffee will be consumed differently from a mug than if room temperature water were consumed from that same mug. Through machine learning, it is possible to detect the type of drink by knowing the container type and how the user tends to consume different types of beverages. For example, a user could drink either hot tea or coffee from a typical coffee mug. After logging multiple events during which he drank hot tea and coffee from a similar mug, the program can learn slight differences in the way they are consumed. One way this could be performed is by detecting and analyzing number of sips and/or duration of sips. The duration of each sip of hot tea might be longer and more gradual resulting in a reduced slope of the x axis acceleration during consumption (Step 5) when compared to coffee. From the container recognition, the program will know what type of fluid container the beverage is being consumed from. Based on such information, the program can narrow the possible drinks to a limited number of possibilities. After collecting data from the specific user, the program will learn how the user drinks each type of beverage differently. The program can assign the type of drink automatically, negating the need for the user to enter the type of drink they are consuming. To ensure accuracy and help with learning, the program could give the user the option to edit or change the type of drink consumed after the event has occurred.

Knowing the type of drink is necessary when applying nutritional information to the consumption of any fluid. Either through user input or through the container and drink recognition algorithm described above, each sip and or complete drink will be marked with the type of fluid the user consumed. Through either information stored on a remote server in the cloud, through information stored on the device, or information stored on a peripheral electronic device, each sip and/or completed beverage can be marked with the type of drink and nutritional information. By knowing the type of drink, the nutritional information relating to that type of drink, and the quantity consumed, the user will be able to look up nutritional information of their complete fluid consumption over any period of time.

In any of the algorithms used, there are many tools to help with the analysis of the raw, preprocessed, or post processed data. For example, the descriptions above specifically mention running a linear regression on the peak accelerations from sips throughout the entire beverage in order to determine the type of container. The description for the final sip detection mentions multiple ways in determining when the final sip has occurred by looking at the magnitude of the peak acceleration, difference between sequential peaks, and other methods. Some other useful tools for any of the algorithms include, but are not limited to, running parametric models (e.g., Autoregressive models), Fourier Transforms, Fast Fourier Transforms, Stochastic estimations, Linear Predictive Analysis, and other filtering techniques (e.g., Least Mean Squares, Kalaman, etc.).

With any of the algorithms used, applying machine learning can result in much more accurate prediction and detection of desired information (e.g., the consumption process, the final sip, the type of container, the type of beverage, etc.). When the user is active in marking when a sip is taken, for instance from a secondary drink or when the user marks the exact type of beverage consumed, the data gathered can be used as training data to improve the algorithm through supervised learning techniques such as Random forests. In other situations, machine learning can be used to better understand the individual user, and adapt the algorithms to that user's specific habits and movements by looking at patterns over time.

Other substantially and specifically practical and useful embodiments may become apparent to those skilled in this art from reading the above-recited and/or herein-included detailed description and/or drawings of certain exemplary embodiments. It should be understood that numerous variations, modifications, and additional embodiments are possible, and accordingly, all such variations, modifications, and embodiments are to be regarded as being within the scope of this application.

The invention claimed is:

1. A method for detecting when a user is consuming fluid during an individual sip, comprising:
   providing an electronic device capable of being worn on an extremity of a user, detecting movement, position, or orientation of said electronic device and said extremity by way of a motion sensor provided by said electronic device, receiving and analyzing signals from said motion sensor by way of a microprocessor capable of running a programmed algorithm, detecting when the user performs one or more actions that indicate the user is consuming a fluid during an individual sip by isolating and marking a start of actual fluid consumption when a tilting action is recognized and marking an end of actual fluid consumption when an untilting action is recognized, using said programmed algorithm, wherein the tilting and/or untilting action is recognized by comparing a standard deviation of a total acceleration (total g) of the electronic device for a set period of time to individual accelerations of one or more x-, y-, or z-axes, position, change in the x-axis acceleration, or orientation of said user's extremity and/or said electronic device and wherein the total acceleration is determined by: total $g = \sqrt{x^2 + y^2 + z^2}$ where x, y, and z are the individual accelerations of the x-, y-, and z-axes, respectively, wherein the tilting action is recognized by the following criteria:
a) a root mean square of the y-axis acceleration and the z-axis acceleration is greater than 0.5 g and less than 1.4 g;
b) the total acceleration is greater than 0.8 g and less than 1.2 g and/or the standard deviation of the total acceleration is less than 0.05 g within a window equal to or less than 1 second; and
c) a change in the x-axis acceleration is greater than 0 g and less than 1.1 g every 1 second.

2. The method of claim 1, wherein said programmed algorithm is capable of recognizing specific gestures of said extremity and filtering out non-drinking movements in determining whether said user is consuming a fluid.

3. The method of claim 1, wherein said programmed algorithm is capable of isolating when fluid is being consumed by the user and analyzing information from this consumption period to determine certain drinking behaviors.

4. The method of claim 1, wherein a change in position or orientation is recognized by way of at least one gyroscope and/or at least one accelerometer provided by said electronic device.

5. The method of claim 1, wherein said motion sensor comprises a gyroscope and/or accelerometer and the one or more actions are recognized by analyzing specific movements, orientations or positions of said user's extremity and said electronic device.

6. The method of claim 1, wherein said programmed algorithm is capable of comparing overall movement of said user's extremity and said electronic device to changes in position or orientation of said extremity and said electronic device.

7. The method of claim 1, wherein a change in position or orientation of said extremity and said electronic device is determined by monitoring pitch angle or rotation about an axis parallel to said user's extremity which is a forearm.

8. The method of claim 1, wherein a change in position or orientation of said extremity and said electronic device is determined by monitoring x, y, or z axis accelerations and total accelerations of said extremity and said electronic device.

9. The method of claim 1, wherein one or more of the following gestures are detected to indicate whether said user is drinking:
i) Reaching for drink;
ii) Grabbing drink;
iii) Lifting drink to mouth;
iv) Tilting until liquid touches lips;
v) Tilting while consuming;
vi) Untilting by reversing the drinking tilt to normal holding position;
vii) Lowering drink; and
viii) Returning drink and arm.

10. The method of claim 1, wherein said microprocessor produces information that is provided to said user as results of said analyzing or a summary thereof.

11. The method of claim 1, wherein said microprocessor produces information that is provided to said user to present consequences of drinking behavior of said user based on metrics related to physical performance, as well as physical and/or mental health issues impacted by drinking behavior.

12. The method of claim 1, wherein detecting when said user is consuming a fluid is based on a standard deviation of the total acceleration of below 0.15 g within a window equal to or less than 1 second.

13. The method of claim 8, wherein the root mean square of the y and z axes are used to determine whether said user has lifted said extremity to a drinking position near the user's mouth.

14. The method of claim 1, further comprising estimating the amount of fluid consumed during the individual sip based on the magnitude of measured x-axis accelerations, allowing for peak x-axis acceleration measurements ranging from −0.8 g to 1 g.

15. The method of claim 1, further comprising estimating the amount of fluid consumed during the individual sip based on a duration of the individual sip and a rate of tilt in the x-axis.

16. A method for detecting when a user is consuming a fluid during an individual sip and estimating an amount of fluid being consumed, comprising:
providing an electronic device capable of being worn on an extremity of a user,
detecting movement, position, or orientation of said electronic device and said extremity by way of a motion sensor provided by said electronic device,
receiving and analyzing signals from said motion sensor by way of a microprocessor capable of running a programmed algorithm,
detecting whether the user performs one or more actions that indicate the user is preparing to take an individual sip, using said programmed algorithm, wherein the following gestures are detected to indicate the user is preparing to take an individual sip:
i) Lifting drink to mouth;
ii) Tilting until liquid touches lips;
detecting and marking when fluid consumption has begun, using said programmed algorithm to recognize the following gestures:
iii) Tilting while consuming, which is recognized by the following criteria:
a) detecting continuous increases in a measured x-axis acceleration and allowing for measured x-axis accelerations greater than −0.8 g and less than 1 g;
b) a root mean square of a y-axis acceleration and a z-axis acceleration is greater than 0.5 g and less than 1.4 g;

c) a measured total acceleration is greater than 0.8 g and less than 1.2 g and/or a measured total acceleration standard deviation is less than 0.05 g within a window equal to or less than 1 second; and d) a change in the measured x-axis acceleration is greater than 0 g and less than 1.1 g every 1 second;

detecting and marking an end of fluid consumption, using said programmed algorithm to recognize one or more of the following gestures:

iv) Untilting by reversing the drinking tilt to normal holding position;

v) Lowering drink, and calculating the estimate of an amount of fluid consumed during the individual sip by measuring a magnitude of the x-axis accelerations during the tilting while consuming gesture and/or by measuring a duration of the tilting while consuming gesture.

17. The method of claim 16, wherein the untilting action (gesture iv.) is recognized by the following criteria:
    a. A change in the x axis accelerations are less than −0.3 g every 1 second; and
    b. A measured total acceleration is greater than 0.7 g and less than 1.3 g and/or the measured total acceleration standard deviation is less than 0.5 g.

18. The method of claim 16, wherein the lowering drink action (gesture v.) is recognized by the following criteria:
    A minimum measured x axis acceleration within a set period reaches a value below −0.5 g.

19. The method of claim 16, wherein calculating the estimate of the amount of fluid consumed during the individual sip by measuring the magnitude of the x axis accelerations during the tilting while consuming gesture is performed using an average x axis acceleration.

20. The method of claim 16, wherein the amount of the fluid consumed during the individual sip is further calculated by a total change in magnitude of the x axis acceleration during the tilting while consuming gesture.

21. The method of claim 16, wherein the amount of the fluid consumed during the individual sip is further calculated by a rate of change in the x axis acceleration during the tilting while consuming gesture.

22. The method of claim 16, wherein the amount of fluid consumed during the individual sip is further determined by using the sip duration to calculate an average rate of change in the x axis acceleration during the tilting while consuming gesture.

23. The method of claim 16, wherein the lifting drink to mouth action (gesture i.) is recognized by the following criteria:
    a. A minimum x axis acceleration is less than −0.5 g at the beginning of gesture i.;
    b. A measured total acceleration is greater than 0.7 g and less than 1.3 g and/or the measured total acceleration standard deviation is less than 0.5 g;
    c. A change in the x axis acceleration is greater than 0.1 g every 1 second; and
    d. A change in the absolute value of the y axis acceleration is greater than 0.04 g every 1 second.

24. The method of claim 16, wherein the tilting until liquid touches lips gesture (gesture ii) is recognized by the following criteria:
    a. A measured total acceleration is greater than 0.7 g and less than 1.3 g and/or the measured total acceleration standard deviation is less than 0.5 g;
    b. A change in the x axis acceleration is greater than 0.1 g every 1 second; and
    c. A change in the absolute value of the y axis acceleration is less than 0.04 g every 1 second.

25. The method of claim 24, wherein the minimum x axis acceleration over a time period of no longer than 10 seconds prior to fluid consumption is used to determine if a lifting or tilting event has occurred prior to a consumption phase.

26. An apparatus comprising:
    A device capable of being worn on an extremity by a user, wherein the device comprises a motion sensor, microprocessor, and programmed algorithm, and wherein the device is capable of being programmed to detect when the user is taking an individual sip, and to detect an amount of fluid consumed, comprising:

detecting movement, position, or orientation of the device and said extremity by way of said motion sensor provided by said device, receiving and analyzing signals from said motion sensor by way of said microprocessor capable of running said programmed algorithm, and detecting when the user performs one or more actions that indicate the user is consuming a fluid by determining and marking when the user starts consuming the fluid during the individual sip and when the user stops consuming the fluid during the individual sip, using said programmed algorithm, wherein said one or more actions are recognized by the following criteria:

a) comparing total acceleration (total g) of the device to individual accelerations of one or more x-, y-, or z-axes, position, or orientation of said user's extremity and/or said device and wherein the total acceleration is determined by: total $g=\sqrt{x^2+y^2+z^2}$ where x, y, and z are the individual accelerations of the x-, y-, and z-axes, respectively;

b) a root mean square of a y-axis acceleration and a z-axis acceleration is greater than 0.5 g and less than 1.4 g;

c) the total acceleration is greater than 0.8 g and less than 1.2 g and/or a total acceleration standard deviation is less than 0.05 g within a window equal to or less than 1 second; and d) a change in an x-axis acceleration is greater than 0 g and less than 1.1 g every 1 second;

wherein the amount of fluid being consumed is calculated based on a magnitude of the x-axis accelerations between the marked start of the fluid consumption and the marked end of the fluid consumption, wherein a sip is capable of being detected between −0.8 g and 1 s.

* * * * *